US007074783B2

(12) United States Patent
Holcomb et al.

(10) Patent No.: US 7,074,783 B2
(45) Date of Patent: Jul. 11, 2006

(54) SULFONYLBENZODIAZEPINONE ACETAMIDES AS BRADYKININ ANTAGONISTS

(75) Inventors: Ryan C. Holcomb, Bellevue, WA (US); Francine S. Grant, Bellevue, WA (US); Michael A. Pleiss, Sunnyvale, CA (US); Eugene D. Thorsett, Half Moon Bay, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 162 days.

(21) Appl. No.: 10/685,353

(22) Filed: Oct. 9, 2003

(65) Prior Publication Data
US 2004/0138208 A1   Jul. 15, 2004

Related U.S. Application Data

(60) Provisional application No. 60/417,165, filed on Oct. 10, 2002.

(51) Int. Cl.
C07D 243/24 (2006.01)
A61K 31/55 (2006.01)
(52) U.S. Cl. .................. 514/221; 540/512; 540/513
(58) Field of Classification Search ............ 540/512, 540/513; 514/221
See application file for complete search history.

(56) References Cited

U.S. PATENT DOCUMENTS 3,654,275 A   4/1972   McManus

FOREIGN PATENT DOCUMENTS

| DE | 43 41 663 A1 | 6/1995 |
| WO | 02/099388 A2 | 12/2002 |
| WO | 03/007958 A1 | 1/2003 |
| WO | 2004/033436 A1 | 4/2003 |
| WO | 03/093245 A1 | 11/2003 |

OTHER PUBLICATIONS

Menke, et al., "Expression Cloning of a Human $B_1$ Bradykinin Receptor", J. Biol. Chem., 269(34):21583-21586 (1994).
Hess, et al., "Cloning and Pharmacological Characterization of a Human Bradykinin (BK-2) Receptor", Biochem Biophys. Res. Commun., 184:260-268 (1992).
Burch, et al., "Bradykinin Receptor Antagonists", Med., 30:237-269 (1990).
Ammons, et al., "Effects of Intracardiac Bradykinin on $T_2$-$T_5$ Medial Spinothalamic Cells", The American Physiological Society, 0363-6119, R147-R152 (1985).
Costello, et al., "Suppression of Carageenan-Induced Hyperalgesia, Hyperthermia and Edema by a Bradykinin Antagonist", European Journal of Pharmacology, 171:259-263 (1989).
Laneuville, et al., "Bradykinin Analogue Blocks Bradykinin-induced Inhibition of a Spinal Nociceptive Reflex in the Rat", European Journal of Pharmacology, 137:281-285 (1987).
Steranka, et al., "Antinociceptive Effects of Bradykinin Antagonists", European Journal of Pharmacology, 136:261-262 (1987).
Steranka, et al., "Bradykinin as a Pain Mediator: Receptors are Localized to Sensory Neurons, and Antagonists have Analgesic Actions", Neurobiology, 85:3245-3249 (1988).
Whalley, et al., "The Effect of Kinin Agonists and Antagonists on the Pain Response of the Human Blister Base", Naunyn Schmiederberg's Arch. Pharmacol., 336:652-655 (1987).
Back, et al., "Determination of Components of the Kallikrein-Kinin System in the Cerebrospinal Fluid of Patients with Various Diseases", Res. Clin. Stud. Headaches, 3:219-226 (1972).
Ness, et al., "Visceral Pain: a Review of Experimental Studies", Pain, 41:167-234 (1990).
Aasen, et al., "Plasma kallikrein Activity and Prekallikrein Levels during Endotoxin Shock in Dogs", Eur. Surg. Res., 10:50-62(1978).
Aasen, et al., "Plasma Kallikrein-Kinin System in Septicemia", Arch. Surg., 118:343-346 (1983).
Katori, et al., "Evidence for the Involvement of a Plasma Kallikrein-Kinin System in the Immediate Hypotension Produced by Endotoxin in Anaesthetized Rats", Br. J. Pharmacol., 98:1383-1391 (1989).
Marceau, et al., "Pharmacology of Kinins: Their Relevance to Tissue Injury and Inflammation", Gen. Pharmacol., 14:209-229 (1983).
Weipert, et al., "Attenuation of arterial blood pressure fall endotoxin shock in the rat using the competitive bradykinin antagonist Lys-Lys-[Hyp$^2$, Thi$^{5,8}$, DPhe$^7$]-BK (B4148)", Brit J. Pharm., 94:282-284 (1988).
Haberland, "The Role of Kininogenases, Kinin Formation and Kininogenase Inhibition in Post Traumatic Shock and Related Conditions", Klinische Woochen-Schrift, 56:325-331 (1978).
Ellis, et al., "Inhibition of Bradykinin-and Kallikrein-Induced Cerebral Arteriolar Dilation by Specific Bradykinin Antagonist", Stroke, 18:792-795 (1987).
Kamitani, et al., "Evidence for a Possible Role of the Brain Kallikrein-Kinin System in the Modulation of the Cerebral Circulation", Circ. Res., 57:545-552 (1985).

(Continued)

Primary Examiner—Bruck Kifle
(74) Attorney, Agent, or Firm—Foley & Lardner LLP

(57) ABSTRACT

Disclosed are compounds, which are bradykinin antagonists and are useful to treat diseases or relieve adverse symptoms associated with disease conditions in mammals mediated by bradykinin. Certain of the compounds exhibit increased potency and are expected to also exhibit an increased duration of action.

12 Claims, No Drawings

OTHER PUBLICATIONS

Barnes, "Inflammatory Mediator Receptors and Asthma", Am. Rev. Respir. Dis., 135:S26-S31 (1987).

Burch, et al., "Bradykinin Receptor Antagonists", Med Res. Reviews., 10::237-269 (1990).

Fuller, et al., "Bradykinin-induced Bronchoconstriction in Humans", Am. Rev. Respir. Dis., 135:176-180 (1987).

Jin, et al., "Inhibition of Bradykinin-Induced Bronchoconstriction in the Guinea-Pig by a Synthetic $B_2$ Receptor Antagonist", Br. J. Pharmacol., 97:598-602 (1989).

Polosa, et al., "Contribution of Histamine and Prostanoids to Bronchoconstriction Provoked by Inhaled Bradykinin in Atopic Asthma", Allergy, 45:174-182 (1990).

Baumgarten, et al., "Concentrations of Glandular Kallikrein in Human Nasal Secretions Increase During Experimentally Induced Allergic Rhinitis", J. Immunology, 137:1323-1328 (1986).

Proud, et al., "Nasal Provocation with Bradykinin Induces Symptoms of Rhinitis and a Sore Throat", Am. Rev. Respir Dis., 137:613-616 (1988).

Seabrook, et al., "Expression of $B_1$ and $B_2$ Bradykinin Receptor mRNA and Their Functional Roles in Sympathetic Ganglia and Sensory Dorsal Root Ganglia Neurons from Wild-type and $B_2$ Receptor Knockout Mice", Neuropharmacology, 36(7):1009-17 (1997).

Elguero, et al., Nonconventional Analgesics: Bradykinin Antagonists, An. Real. Acad. Farm., 63:173-190 (1997).

Artis, et al., "Structured-based design of Six novel classes of nonpeptide antagonists of the bradykinin $B_2$ receptor", Bioganic & Med. Chem. Letters, 10:2421-2425, (2000).

Dziadulewicz, et al., "The design of non-peptide human bradykinin $B_2$ receptor antagonists employing the benzodiazepine peptidomimetic scaffold", Bioganic & Med. Chem. Letters, 9:463-468, (1999).

SULFONYLBENZODIAZEPINONE ACETAMIDES AS BRADYKININ ANTAGONISTS

CROSS REFERENCE TO RELATED APPLICATIONS

This application claims the benefit under 35 U.S.C. §119 (e) of U.S. Provisional Application No. 60/417,165, filed Oct. 10, 2002, which is hereby incorporated by reference in its entirety.

BACKGROUND OF THE INVENTION

1. Field of the Invention

This invention is directed to certain sulfonylbenzodiazepinone acetamide derivatives and related compounds. These compounds are useful as bradykinin antagonists to relieve adverse symptoms in mammals mediated, at least in part, by bradykinin including pain, inflammation, bronchoconstriction, cerebral edema, etc.

2. References

The following literature and patent publications are cited in this application as superscript numbers.

1. Menke, et al., J. Biol. Chem., 269(34):21583–2158 (1994).
2. Hess, Biochem. Human B2 Receptor, Biophys. Res. Commun., 184:260–268 (1992)
3. Burch, et al., "Bradykinin Receptor Antagonists", J. Med. Chem., 30:237–269 (1990).
4. Clark, "Kinins and the Peripheral Central Nervous Systems", Handbook of Experimental Pharmacology, Vol. XXV: Bradykinin, Kallidin, and Kallikrein. Erdo, E. G. (Ed.), 311–322 (1979).
5. Ammons, et al., "Effects of Intracardiac Bradykinin on T2–T5 Medial Spinothalamic Cells", The American Physiological Society, 0363–6119 (1985).
6. Costello, et al., "Suppression of Carageenan-Induced Hyperalgesia, Hyperthermia and Edema by a Bradykinin Antagonist", European Journal of Pharmacology, 171:259–263 (1989).
7. Laneuville, et al., "Bradykinin Analogue Blocks Bradykinin-induced Inhibition of a Spinal Nociceptive Reflex in the Rat", European Journal of Pharmacology, 137: 281–285 (1987).
8. Steranka, et al., "Antinociceptive Effects of Bradykinin Antagonists", European Journal of Pharmacology, 16:261–262 (1987).
9. Steranka, et al., "Bradykinin as a Pain Mediator: Receptors are Localized to Sensory Neurons, and Antagonists have Analgesic Actions", Neurobiology, 85:3245–3249 (1987).
10. Whalley, et al., in Naunyn Schmiederberg's Arch. Pharmacol., 336:652–655 (1987).
11. Back, et al., "Determination of Components of the Kallikrein-Kinin System in the Cerebrospinal Fluid of Patients with Various Diseases", Res. Clin. Stud. Headaches, 3:219–226 (1972).
12. Ness, et al., "Visceral pain: a Review of Experimental Studies", Pain, 41:167–234 (1990).
13. Aasen, et al., "Plasma kallikrein Activity and Prekallikrein Levels during Endotoxin Shock in Dogs", Eur. Surg., 10:5062(1977).
14. Aasen, et al., "Plasma Kallikrein-Kinin System in Septicemia", Arch. Surg., 118:343–346 (1983).
15. Katori, et al., "Evidence for the Involvement of a Plasma Kallikrein/Kinin System in the Immediate Hypotension Produced by Endotoxin in Anaesthetized Rats", Br. J. Pharmacol., 98:1383–1391 (1989).
16. Marceau, et al., "Pharmacology of Kinins: Their Relevance to Tissue Injury and Inflammation", Gen. Pharmacol., 14:209–229 (1982).
17. Weipert, et al., Brit J. Pharm., 94:282–284 (1988).
18. Haberland, "The Role of Kininogenases, Kinin Formation and Kininogenase Inhibitor in Post Traumatic Shock and Related Conditions", Klinische Woochen-Schrift, 56:325–331 (1978).
19. Ellis, et al., "Inhibition of Bradykinin-and Kallikrein-Induced Cerebral Arteriolar Dilation by Specific Bradykinin Antagonist", Stroke, 18:792–795 (1987).
20. Kamitani, et al., "Evidence for a Possible Role of the Brain Kallikrein-Kinin System in the Modulation of the Cerebral Circulation", Circ. Res., 57:545–552 (1985).
21. Barnes, "Inflammatory Mediator Receptors and Asthma", Am. Rev. Respir. Dis., 135:S26–S31 (1987).
22. Burch, et al., "Bradykinin Receptor Antagonists", J. Med. Chem., 30:237–269 (1990).
23. Fuller, et al., "Bradykinin-induced Bronchoconstriction in Humans", Am. Rev. Respir. Dis., 135:176–180 (1987).
24. Jin, et al., "Inhibition of Bradykinin-Induced Bronchoconstriction in the Guinea-Pig by a Synthetic B2 Receptor Antagonist", Br. J. Pharmacol., 97:598–602 (1989).
25. Polosa, et al., "Contribution of Histamine and Prostanoids to Bronchoconstriction Provoked by Inhaled Bradykinin in Atopic Asthma", Allergy, 45:174–182 (1990).
26. Baumgarten, et al., "Concentrations of Glandular Kallikrein in Human Nasal Secretions Increase During Experimentally Induced Allergic Rhinitis", J. Immunology, 137:1323–1328 (1986).
27. Proud, et al., "Nasal Provocation with Bradykinin Induces Symptoms of Rhinitis and a Sore Throat", Am. Rev. Respir Dis., 137:613–616 (1988).
28. Steward and Vavrek in "Chemistry of Peptide Bradykinin Antagonists" Basic and Chemical Research, R. M. Burch (Ed.), pages 51–96 (1991).
29. Seabrook, et al., Expression of B1 and B2 Bradykinin Receptor mRNA and Their Functional Roles in Sympathetic Ganglia and Sensory Dorsal Root Ganglia Neurons from Wild-type and B2 Receptor Knockout Mice, Neuropharmacology, 36(7):1009–17 (1997).
30. Elguero, et al., Nonconventional Analgesics: Bradykinin Antagonists, An. R. Acad. Farm., 63(1):173–90 (Spa) (1997).
31. McManus, U.S. Pat. No. 3,654,275, Quinoxalinecarboxamide Antiinflammatory Agents, issued Apr. 4, 1972.
32. Grant, et al., U.S. patent application Ser. No. 10/429, 203, Sulfonylquinoxalone Acetamide Derivatives and Related Compounds as Bradykinin Antagonists, filed May 3, 2003.
33. Grant, et al., U.S. patent application Ser. No. 10/429, 917, Sulfonylquinoxalone Acetamide Derivatives and Related Compounds as Bradykinin Antagonists, filed May 3, 2003.

All of the above identified publications are herein incorporated by reference in their entirety to the same extent as if each individual publication was specifically and individually incorporated by reference in its entirety.

State of the Art

Bradykinin (BK) is known to be one of the most potent naturally occurring simulators of C-fiber afferents mediating pain. It also is a potent vasodilator, edema-producing agent, and stimulator of various vascular and non-vascular smooth muscles in tissues such as uterus, gut and bronchiole. The kinin/kininogen activation pathway has also been described as playing a pivotal role in a variety of physiological and pathophysiological processes, being one of the first systems to be activated in the inflammatory response and one of the most potent simulators of: (i) phospholipase A2 and, hence, the generation of prostaglandins and leukotrienes; and (ii) phospholipase C and thus, the release of inositol phosphates and diacylglycerol. These effects are mediated predominantly via activation of BK receptors of the BK2 type.

Bradykinin (BK) is a peptide composed of nine amino acids (Arg1-Pro2-Pro3-Gly4-Phe5-Ser6-Pro7-Phe8-Arg9) (SEQ. ID. NO. 1) which, along with lysyl-BK (kallidin), is released from precursor kininogens by proteases termed kallikreins. Plasma kallikrein circulates as an inactive zymogen, from which active kallikrein is released by Hageman factor. Tissue kallikrein appears to be located predominantly on the outer surface of epithelial cell membranes at sites thought to be involved in transcellular electrolyte transport.

B2 receptors are receptors for bradykinin and kallidin; they predominate and are normally found in most tissues. B1 receptors are specific for [des-Arg9] bradykinin and [des-Arg10] kallidin. The B1 subtype is induced by inflammatory processes. Bradykinin receptors have been cloned for different species, notably the human B1 receptor. See, Menke, et al.[1] and Hess.[2]

The distribution of receptor B1 is very limited since this receptor is only expressed during states of inflammation. Two generations of peptidic antagonists of the B2 receptor have been developed. The second generation has compounds two orders of magnitude more potent as analgesics than first generation compounds and the most important derivative was icatibant. The first non-peptidic antagonist of the B2 receptor, described in 1993, has two phosphonium cations separated by a modified amino acid. Many derivatives of this di-cationic compound have been prepared. Another non-peptidic compound antagonist of B2 is the natural product Martinelline. See, Elguero.[30] See also, Seabrook.[29]

Two major kinin precursor proteins, high molecular weight and low molecular weight kininogen are synthesized in the liver, circulate in plasma, and are found in secretions such as urine and nasal fluid. High molecular weight kininogen is cleaved by plasma kallikrein, yielding BK, or by tissue kallikrein, yielding kallidin. However, low molecular weight kininogen is a substrate only for tissue kallikrein. In addition, some conversion of kallidin to BK may occur inasmuch as the amino terminal lysine residue of kallidin is removed by plasma aminopeptidases. Plasma half-lives for kinins are approximately 15 seconds, with a single passage through the pulmonary vascular bed resulting in 80–90% destruction. The principle catabolic enzyme in vascular beds is the dipeptidyl carboxypeptidase kininase II or angiotensin-converting enzyme (ACE). A slower acting enzyme, kininase I, or carboxypeptidase N, which removes the carboxyl terminal Arg, circulates in plasma in great abundance. This suggests that it may be the more important catabolic enzyme physiologically. Des-Arg9-bradykinin as well as des-Arg10-kallidin formed by kininase I acting on BK or kallidin, respectively, are acting BK1 receptor agonists, but are relatively inactive at the more abundant BK2 receptor at which both BK and kallidin are potent agonists.

Direct application of bradykinin to denuded skin or intra-arterial or visceral injection results in the sensation of pain in mammals including humans. Kinin-like materials have been isolated from inflammatory sites produced by a variety of stimuli. In addition, bradykinin receptors have been localized to nociceptive peripheral nerve pathways and BK has been demonstrated to stimulate central fibers mediating pain sensation. Bradykinin has also been shown to be capable of causing hyperalgesia in animal models of pain. See, Burch, et al.[3] and Clark.[4]

These observations have led to considerable attention being focused on the use of BK antagonists as analgesics. A number of studies have demonstrated that bradykinin antagonists are capable of blocking or ameliorating both pain as well as hyperalgesia in mammals including humans. See, Ammons et al.,[5] Clark[4], Costello, et al.,[6] Laneuville, et al.,[7] Steranka, et al.,[8] and Steranka, et al.[9]

Currently accepted therapeutic approaches to analgesia have significant limitations. While mild to moderate pain can be alleviated with the use of non-steroidal anti-inflammatory drugs and other mild analgesics, severe pain such as that accompanying surgical procedures, burns and severe trauma requires the use of narcotic analgesics. These drugs carry the limitations of abuse potential, physical and psychological dependence, altered mental status and respiratory depression which significantly limit their usefulness.

Prior efforts in the field of BK antagonists indicate that such antagonists can be useful in a variety of roles. These include use in the treatment of burns, perioperative pain, migraine and other forms of pain, shock, central nervous system injury, asthma, rhinitis, premature labor, inflammatory arthritis, inflammatory bowel disease, neuropathic pain, etc. For example, Whalley, et al. has demonstrated that BK antagonists are capable of blocking BK-induced pain in a human blister base model.[10] This suggests that topical application of such antagonists would be capable of inhibiting pain in burned skin, e.g., in severely burned patients that require large doses of narcotics over long periods of time and for the local treatment of relatively minor burns or other forms of local skin injury.

The management of perioperative pain requires the use of adequate doses of narcotic analgesics to alleviate pain while not inducing excessive respiratory depression. Post-operative narcotic-induced hypoventilation predisposes patients to collapse of segments of the lungs, a common cause of post-operative fever, and frequently delays discontinuation of mechanical ventilation. The availability of a potent non-narcotic parenteral analgesic could be a significant addition to the treatment of perioperative pain. While no currently available BK antagonist has the appropriate pharmacodynamic profile to be used for the management of chronic pain, frequent dosing and continuous infusions are already commonly used by anesthesiologists and surgeons in the management of perioperative pain.

Several lines of evidence suggest that the kallikrein/kinin pathway may be involved in the initiation or amplification of vascular reactivity and sterile inflammation in migraine. See, Back, et al.[11] Because of the limited success of both prophylactic and non-narcotic therapeutic regimens for migraine as well as the potential for narcotic dependence in these patients, the use of BK antagonists offers a highly desirable alternative approach to the therapy of migraine.

Bradykinin is produced during tissue injury and can be found in coronary sinus blood after experimental occlusion of the coronary arteries. In addition, when directly injected into the peritoneal cavity, BK produces a visceral type of pain. See, Ness, et al.[12] While multiple other mediators are also clearly involved in the production of pain and hyperalgesia in settings other than those described above, it is also believed that antagonists of BK have a place in the alleviation of such forms of pain as well.

Shock related to bacterial infections is a major health problem. It is estimated that 400,000 cases of bacterial sepsis occur in the United States yearly, of those 200,000 progress to shock, and 50% of these patients die. Current therapy is supportive, with some suggestion in recent studies that monoclonal antibodies to Gram-negative endotoxin may have a positive effect on disease outcome. Mortality is still high, even in the face of this specific therapy, and a significant percentage of patients with sepsis are infected with Gram-positive organisms which would not be amenable to anti-endotoxin therapy.

Multiple studies have suggested a role for the kallikrein/kinin system in the production of shock associated with endotoxin. See, Aasen, et al.,[13] Aasen, et al.,[14] Katori, et al.[15] and Marceau, et al.[16] Recent studies using newly available BK antagonists have demonstrated in animal models that these compounds can profoundly affect the progress of endotoxic shock. See, Weipert, et al.[17] Less data is available regarding the role of BK and other mediators in the production of septic shock due to Gram-positive organisms. However, it appears likely that similar mechanisms are involved. Shock secondary to trauma, while frequently due to blood loss, is also accompanied by activation of the kallikrein/kinin system. See, Haberland.[18]

Numerous studies have also demonstrated significant levels of activity of the kallikrein/kinin system in the brain. Both kallikrein and BK dilate cerebral vessels in animal models of CNS injury. See Ellis, et al.[19] and Kamitani, et al.[20] Bradykinin antagonists have also been shown to reduce cerebral edema in animals after brain trauma. Based on the above, it is believed that BK antagonists should be useful in the management of stroke and head trauma.

Other studies have demonstrated that BK receptors are present in the lung, that BK can cause bronchoconstriction in both animals and man and that a heightened sensitivity to the bronchoconstrictive effect of BK is present in asthmatics. Some studies have been able to demonstrate inhibition of both BK and allergen-induced bronchoconstriction in animal models using BK antagonists. These studies indicate a potential role for the use of BK antagonists as clinical agents in the treatment of asthma. See Barnes,[21] Burch, et al.,[22] Fuller, et al.,[23] Jin, et al.[24] and Polosa, et al.[25] Bradykinin has also been implicated in the production of histamine and prostanoids to bronchoconstriction provoked by inhaled bradykinin in atopic asthma.[25] Bradykinin has also been implicated in the production of symptoms in both allergic and viral rhinitis. These studies include the demonstration of both kallikrein and BK in nasal lavage fluids and that levels of these substances correlate well with symptoms of rhinitis. See, Baumgarten, et al.,[26] Jin, et al., and Proud, et al.[27]

In addition, studies have demonstrated that BK itself can cause symptoms of rhinitis. Stewart and Vavrek[28] discuss peptide BK antagonists and their possible use against effects of BK. A great deal of research effort has been expended towards developing such antagonists with improved properties. However, notwithstanding extensive efforts to find such improved BK antagonists, there remains a need for additional and more effective BK antagonists. Two of the major problems with presently available BK antagonists are their low levels of potency and their extremely short durations of activity. Thus there is a special need for BK antagonists having increased potency and for duration of action.

U.S. Pat. No. 3,654,275 teaches that certain 1,2,3,4-tetrahydro-1-acyl-3-oxo-2-quinoxalinecarboxamides have anti-inflammatory activity and describes the preparation of certain intermediates which can also be used as intermediates in the preparation of the compounds hereafter described.[31]

In addition, Grant, et al., U.S. patent application Ser. No. 10/429,203, Sulfonylquinoxalone Acetamide Derivatives and Related Compounds as Bradykinin Antagonists, filed May 3, 2003 and Grant, et al., U.S. patent application Ser. No. 10/429,917, Sulfonylquinoxalone Acetamide Derivatives and Related Compounds as Bradykinin Antagonists, filed May 3, 2003 disclose a variety of sulfonylquinoxalone acetamide derivatives as BK antagonists.[32,33]

In view of the above, compounds which are bradykinin antagonists would be particularly advantageous in treating those diseases mediated by bradykinin.

SUMMARY OF THE INVENTION

This invention is directed, in part, to compounds which are bradykinin antagonists and are useful to treat diseases or relieve adverse symptoms associated with disease conditions in mammals mediated by bradykinin. Certain of the compounds exhibit increased potency and are expected to also exhibit an increased duration of action.

The present invention provides for compounds of Formula I:

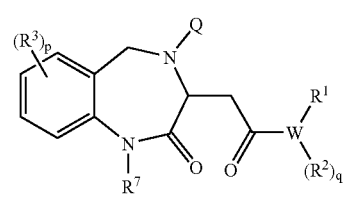

Q is selected from the group consisting of —SO₂R and —CH₂C(O)R;

W is selected from the group consisting of O, S, and N, wherein when W is O or S, then q is zero and when W is N, then q is one;

R is selected from the group consisting of aryl, substituted aryl, heteroaryl, substituted heteroaryl, heterocyclic and substituted heterocyclic;

R¹ and R² are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic, or R¹ and R² together with the nitrogen atom to which they are attached form a heteroaryl, substituted heteroaryl, heterocyclic, or substituted heterocyclic;

each R³ is independently selected from the group consisting of alkyl, substituted alkyl, alkenyl, substituted alkenyl, alkynyl, substituted alkynyl, amino, substituted amino, acylamino, aminoacyl, cycloalkyl, substituted cycloalkyl, alkoxy, substituted alkoxy, aryl, substituted aryl, aryloxy, substituted aryloxy, heteroaryl, substituted heteroaryl, heteroaryloxy, substituted heteroaryloxy, heterocyclic, substituted heterocyclic, heterocyclyloxy, substituted heterocyclyloxy, acyl, acyloxy, halogen, nitro, cyano, hydroxy, carboxy, and carboxyl esters;

or two or more of $R^3$ together with the carbon atoms to which they are joined form a fused ring cycloalkenyl, substituted cycloalkenyl, aryl, substituted aryl, heteroaryl, substituted heteroaryl, unsaturated heterocyclic or substituted unsaturated heterocyclic;

$R^7$ is selected from the group consisting of hydrogen, alkyl, substituted alkyl, alkenyl, substituted alkenyl, cycloalkyl, substituted cycloalkyl, aryl, substituted aryl, heteroaryl, substituted heteroaryl, heterocyclic, substituted heterocyclic, acyl and acyloxy;

or $R^7$ together with at least one of $R^3$ and the nitrogen and carbon atoms to which they are joined forms a fused ring heteroaryl, substituted heteroaryl, unsaturated heterocyclic or substituted unsaturated heterocyclic;

p is an integer of from 0 to 3;

or pharmaceutically acceptable salts, prodrugs, tautomers or isomers thereof.

Preferred R groups include, for example, phenyl, naphth-1-yl, 5-dimethylaminonaphth-1-yl, 2-fluorophenyl, 2-chlorophenyl, 2-cyanophenyl, 2-methylphenyl, 2-nitrophenyl, 2-trifluoromethylphenyl, 3-chlorophenyl, 4-methylphenyl (tolyl), 2,5-dibromophenyl, 4-bromo-2-ethylphenyl, 4-bromo-2-trifluoromethoxyphenyl, 2,3-dichlorophenyl, 2,4-dichlorophenyl, 3,4-dichlorophenyl, 2,5-dichlorophenyl, 3,5-dichlorophenyl, 2,6-dichlorophenyl, 2-chloro-4-cyanophenyl, 2-chloro-4-fluorophenyl, 3-chloro-2-methylphenyl, 2-chloro-6-methylphenyl, 5-chloro-2-methoxyphenyl, 2-chloro-4-trifluoromethylphenyl, 2,4-difluorophenyl, 5-fluoro-2-methylphenyl, 2,5-dimethoxyphenyl, 2-methoxy-4-methylphenyl, 2-methoxy-5-bromophenyl, 2-methoxy-5-methylphenyl, 2,5-dimethylphenyl, 2-methyl-5-nitrophenyl, 3,5-di(trifluoro-methyl)phenyl, 4-bromo-2,5-difluorophenyl, 2,3,4-trichlorophenyl, 2,4,5-trichlorophenyl, 2,4,6-trichlorophenyl, 2,4-dichloro-5-methylphenyl, 4-chloro-2,5-dimethylphenyl, 2,4,6-tri(iso)propylphenyl, 2,4,6-trimethylphenyl, 2,3,5-trimethyl-4-chlorophenyl, 2,3,6-trimethyl-4-methoxyphenyl, 2,3,4,5,6-pentamethylphenyl, 5-chloro-1,3-dimethylpyrazol-4-yl, 2-methoxycarbonylthiophen-3-yl, 2,3-dimethylimidazol-5yl, 2-methylcarbonylamino-4-methylthiazol-5-yl, quinolin-8-yl, thiophen-2-yl, 1-methylimidiazol-4-yl, 3,5-dimethylisoxazol-4-yl, and N-morpholino.

Particularly preferred R groups include 4-chloro-2,5-dimethylphenyl and 2,3-dichlorophenyl.

When W is N, preferred $R^1$ groups include, for example

2-[(4-amidino)phenyl]-1-(R)-(pyrrolidin-N-ylcarbonyl)eth-1-yl,
amino,
2-[N-(α-aminoacetyl)piperid-4-yl]eth-1-yl,
4-aminobenzyl,
2-[4-(aminoethyleneamidino)phenyl]eth-1-yl,
2-[N-(1-amino-1-methylethylcarbonyl)piperid-4-yl]eth-1-yl,
2-(4-aminophenyl)eth-1-yl,
2-aminothiazol-5-ylmethyl,
(2-aminopyrid-4-yl)methyl,
benzyl,
2-bromoeth-1-yl,
1-(S)-carboxamido-2-(indol-3-yl)eth-1-yl,
carboxamidomethyl,
1-carboxamido-2-(S)-methyl-but-1-yl,
1-(S)-carbamoyl-2-(phenyl)eth-1-yl,
1-(R)-carboxamido-2-(phenyl)eth-1-yl,
4-carboxybenzyl,
2-chloroeth-1-yl,
cyanomethyl,
2-(4-cyanophenyl)eth-1-yl,
2-(4-cyanophenyl)-1-(R)-(pyrrolidin-N-ylcarbonyl)eth-1-yl,
2-(4-cyanophenyl)-1-(S)-(pyrrolidin-N-ylcarbonyl)eth-1-yl,
cyclohexyl,
cyclohexylmethyl,
2-(N-cyclopropylpiperidin-4-yl)eth-1-yl,
2-(N-cyclopropylpiperidin-4-yl)-1-(R)-(pyrrolidin-N-ylcarbonyl)eth-1-yl,
1-(R)-1,3-di(benzyloxycarbonyl)prop-1-yl,
1-(S)-1,3-dicarboxamidoprop-1-yl,
(2-dimethylamino)eth-1-yl,
2-[4-(N,N-dimethylamino]phenethyl,
3-(dimethylamino)prop-1-yl,
1-(S)-ethoxycarbonyleth-1-yl,
2-ethoxyphenyl,
ethyl,
1-(R)-(1-N-ethylaminocarbonyl)-4-amino-n-butyl,
1-(S)-(1-N-ethylaminocarbonyl)-4-amino-n-butyl,
1-(R)-(1-N-ethylaminocarbonyl)-5-(t-butoxycarbonylamino)pent-5-yl,
1-(S)-(1-N-ethylaminocarbonyl)-5-(t-butoxycarbonylamino)pent-5-yl,
1-(R)-(1-N-ethylaminocarbonyl)-4-(N-t-butoxycarbonylamino)-n-but-5-yl,
1-(S)-(1-N-ethylaminocarbonyl)-4-(N-t-butoxycarbonylamino)-n-but-5-yl,
1-(R)-(1-N-ethylaminocarbonyl)-5-guanadino-n-pent-5-yl,
1-(S)-(1-N-ethylaminocarbonyl)-5-guanadino-n-pent-5-yl,
1-(R,S)-(1-N-ethylaminocarbonyl)-4-(N-t-butoxycarbonyl)guanadino-n-but-1-yl,
1-(R)-(1-N-ethylaminocarbonyl)-5-(N-t-butoxycarbonylamino)-n-pent-5-yl,
1-(S)-(1-N-ethylaminocarbonyl)-5-(N-t-butoxycarbonylamino)-n-pent-5-yl,
4-fluorophenethyl,
hydrogen,
2-hydroxyeth-1-yl,
2-(4-hydroxyphenyl)-1-(S)-(methoxycarbonyl)eth-1-yl,
2-(4-hydroxyphenyl)-1-(S)-(isopropoxycarbonyl)eth-1-yl,
2-(4-hydroxyphenyl)-1-(R)-(methoxycarbonyl)eth-1-yl,
2-(N-hydroxypyrid-4-yl)eth-1-yl,
2-(imidazol-4-yl)eth-1-yl,
2-[4-(imidazolin-2-yl)phenyl]-1-(R)-(pyrrolidin-1-ylcarbonyl)eth-1-yl,
2-[4-(imidazolin-2-yl)phenyl]eth-1-yl,
2-(indol-3-yl)eth-1-yl,
2-(indol-3-yl)-1-(S)-(methoxycarbonyl)eth-1-yl,
2-(indol-3-yl)-1-(R)-(methoxycarbonyl)eth-1-yl,
iso-propyl,
1-(R)-(isopropoxycarbonyl)-2-(phenyl)eth-1-yl,
methoxy,
4-(methoxycarbonyl)benzyl,
1-(R)-(methoxycarbonyl)eth-1-yl,
methoxycarbonylmethyl,
methoxycarbonylphenylmethyl,
2-methoxyeth-1-yl,
1-(R)-(methoxcarbonyl)-2-(N-methylpiperidin-4-yl)eth-1-yl,
1-(R)-(methoxycarbonyl)-2-(N-methyl-1,2,3,6-tetrahydropyrid-4-yl)eth-1-yl, 2-methoxyphenyl,
1-(R)-(methoxycarbonyl)-2-pyrid-4-yl)eth-1-yl,
methyl,
2-[4-(methylcarbonylamino]phenethyl,
1-(R)-(N-methyl-N-ethylcarbamoyl)-3-(guanadino)prop-1-yl,
2-(4-methylpiperazin-1-yl)eth-1-yl,
(N-methylpiperidin-2-yl)methyl,
2-(N-methylpiperidin-2-yl)eth-1-yl,
2-(N-methylpiperidin-3-yl)eth-1-yl,
2-(N-methylpiperidin-4-yl)eth-1-yl,
2-(N-methylpiperidin-4-yl)-1-(R)-(pyrrolidin-N-ylcarbonyl)eth-1-yl,
2-[(N-methyl)pyrrolidin-2-yl]eth-1-yl,
2-(N-methyl-1,2,5,6-tetrahydropyrid-4-yl)eth-1-yl,
2-(N-methyl-1,2,5,6-tetrahydropyrid-4-yl)-1-(R)-(pyrrolidin-N-ylcarbonyl) eth-1-yl,
3-(2-methylthiazol-5-yl)-pyrazol-5-yl,
2-(N-morpholino)eth-1-yl,
n-hexyl,
4-nitrobenzyl,
phenethyl,
1-(R)-phenyleth-1-yl,
1-(S)-phenyleth-1-yl,
phenyl,
4-phenylbut-1-yl,
1-(R)-2-phenylcarboxyeth-1-yl,
1-(R)-2-phenyl-1-(methoxycarbonyl)eth-1-yl,
1-(S)-2-phenyl-1-(methoxycarbonyl)eth-1-yl,
3-phenyl-n-prop-1-yl,
2-(phenyl)-1-(S)-(pyrrolidin-N-ylcarbonyl)eth-1-yl,
2-(piperidin-N-yl)eth-1-yl,
2-(piperidin-2-yl)eth-1-yl,
2-(piperidin-3-yl)eth-1-yl,
2-(piperidin-4-yl)eth-1-yl,
(piperid-1-yl)carbonylmethyl,
pyrazin-2-ylmethyl,
2-(pyrid-2-yl)eth-1-yl,
2-(pyrid-3-yl)eth-1-yl,
2-(pyrid-4-yl-)eth-1-yl,
(pyrid-2-yl)methyl,
(pyrid-3-yl)methyl,
(pyrid-4-yl)methyl,
2-[N-(pyrid-4-yl)]piperidin-4-yl,
2-[N-(pyrid-4-yl)piperid-4-yl)]eth-1-yl,
2-[N-(pyrid-2-yl)piperid-4-yl]eth-1-yl
2-(pyrid-4-yl)-1-(R)-(pyrrolidin-N-ylcarbonyl)eth-1-yl,
1-(R)-(pyrrolidin-N-ylcarbonyl)-2-(4-amidino)phenyl-eth-1-yl,
1-(S)-(pyrrolidin-N-ylcarbonyl)-2-(4-amidino)phenyl-eth-1-yl,
1-(R)-(pyrrolidin-N-ylcarbonyl)-5-amino-n-pent-1-yl,
1-(S)-(pyrrolidin-N-ylcarbonyl)-5-amino-n-pent-1-yl,
1-(R)-(pyrrolidin-N-ylcarbonyl)-2-(4-biphenyl)eth-1-yl,
1-(S)-(pyrrolidin-N-ylcarbonyl)-2-(4-biphenyl)eth-1-yl,
1-(R)-(pyrrolidin-N-ylcarbonyl-2-(4-iodophenyl)eth-1-yl,
1-(S)-(pyrrolidin-N-ylcarbonyl-2-(4-iodophenyl)eth-1-yl,
1-(R)-(pyrrolidin-N-carbonyl)-4-(t-butoxycarbonylamino)-n-but-1-yl,
1-(S)-(pyrrolidin-N-carbonyl)-4-(t-butoxycarbonylamino)-n-but-1-yl,
1-(S)-(pyrrolidin-N-ylcarbonyl)-2-[4-(2-imidazolin-2-yl)phenyl]eth-1-yl,
2-(R)-(pyrrolidin-N-ylcarbonyl-3-phenylprop-2-yl,
1-(R)-(pyrrolidin-N-ylcarbonyl)-2-[4-(N-methylpiperidin-2-yl)phenyl)]eth-1-yl,
1-(S)-(pyrrolidin-N-ylcarbonyl)-2-[4-(N-methylpiperidin-2-yl)phenyl)]eth-1-yl,
1-(R)-(pyrrolidin-N-ylcarbonyl)-2-[N-methyl-1,2,5,6-tetrahydropyridin-4-yl)-phen-4-yl)]eth-1-yl,
1-(S)-(pyrrolidin-N-ylcarbonyl)-2-[N-methyl-1,2,5,6-tetrahydropyridin-4-yl)-phen-4-yl)]eth-1-yl,
1-(R)-(pyrrolidin-N-ylcarbonyl)-2-[4-(piperidin-2-yl)cyclohexyl)]eth-1-yl,
1-(S)-(pyrrolidin-N-ylcarbonyl)-2-[4-(piperidin-2-yl)cyclohexyl)]eth-1-yl,
1-(R)-(pyrrolidin-N-ylcarbonyl)-2-[N-(phenyl)piperidin-4-yl)]eth-1-yl,
1-(S)-(pyrrolidin-N-ylcarbonyl)-2-[N-(phenyl)piperidin-4-yl)]eth-1-yl,
1-(R)-(pyrrolidin-N-ylcarbonyl)-2-[N-(pyridin-4-yl)piperidin-4-yl)]eth-1-yl,
1-(S)-(pyrrolidin-N-ylcarbonyl)-2-[N-(pyridin-4-yl)piperidin-4-yl)]eth-1-yl,
1-(R)-(pyrrolidin-N-ylcarbonyl)-2-[4-(pyridin-4-yl)phenyl)]eth-1-yl,
1-(S)-(pyrrolidin-N-ylcarbonyl)-2-[4-(pyridin-4-yl)phenyl)]eth-1-yl,
1-(R)-(pyrrolidin-N-ylcarbonyl)-2-[4-(pyrid-2-yl)phenyl]eth-1-yl,
1-(S)-(pyrrolidin-N-ylcarbonyl)-2-[4-(pyrid-2-yl)phenyl]eth-1-yl,
1-(R)-(pyrrolidin-N-ylcarbonyl)-2-[4-(pyrimidin-2-yl)phenyl]eth-1-yl,
1-(S)-(pyrrolidin-N-ylcarbonyl)-2-[4-(pyrimidin-2-yl)phenyl]eth-1-yl,
1-(R)-(pyrrolidin-N-ylcarbonyl)-2-[4-(N-t-butoxycarbonylpyrrol-2-yl)phenyl]eth-1-yl,
1-(S)-(pyrrolidin-N-ylcarbonyl)-2-[4-(N-t-butoxycarbonylpyrrol-2-yl)phenyl]eth-1-yl,
1-(S)-(t-butoxycarbonyl)-2-(4-hydroxyphenyl)eth-1-yl,
3-t-butoxycarbonyl-1-methoxycarbonylprop-1-yl,
2-[N-(t-butoxycarbonylmethyl)piperid-4-yl]eth-1-yl,
2-[1-(t-butoxycarbonylmethyl)piperid-4-yl)]eth-1-yl,
1-(S)-(t-butoxycarbonyl)-3-methylprop-1-yl,
1-(R)-(t-butoxycarbonyl)-3-methylprop-1-yl,
1-(R)-(t-butoxycarbonyl)-2-(phenyl)eth-1-yl,
2-cyclopropyl-2-(pyridin-4-yl)eth-1-yl, and
2-(N-t-butoxycarbonylmethyl)pyridin-4-yl-ethyl.

Particularly preferred $R^1$ groups include, by way of example, 2-(R,S)-[(pyridin-4-yl)]eth-1-yl, 2-(R,S)-[1,2,3,6-tetrahydro-N-methylpyridin-4-yl]eth-1-yl, 2-(R,S)-[N-methylpiperidin-4-yl]eth-1-yl, 2-(R,S)-[N-(pyridin-4-yl)piperidin-4-yl]eth-1-yl, 2-(R,S)-[N-oxopyridin-4-yl]eth-1-yl, 2-(R,S)-cyclopropyl-2-(pyridin-4-yl)eth-1-yl, 2-(R)-(pyridin-4-yl)eth-1-yl, 2-(S)-(pyridin-4-yl)eth-1-yl, and 2-(R,S)-cyclopropyl-2-(pyridin-4-yl)eth-1-yl.

When W is N, preferred $R^2$ groups include hydrogen, methyl, ethyl, iso-propyl, 2-methoxyeth-1-yl, and pyrid-3-ylmethyl.

A particularly preferred $R^2$ group is hydrogen.

In another preferred embodiment, when W is N, $R^1$ and $R^2$ are joined, together with the nitrogen atom to which they are bound, to form an optionally substituted heterocyclic including, by way of example, 4-(2-aminoethyl)piperidin-1-yl, 4-[2-(N-t-butoxycarbonylamino)ethyl]-piperidin-1-yl, 1-(pyridin-2-yl)piperazin-4-yl, N-morpholino, 2-methylpiperid-N-yl, 2-(S)-carboxamide-pyrrolidin-N-yl, 2-(R)-hydroxy-5-(S)-methoxycarbonylpyrrolidin-N-yl, 2-(R)-methoxycarbonyl-pyrrolidin-N-yl, 2-(S)-methoxymethylpyrrolidin-1-yl, 3-(R)-(t-butoxycarboxamido)pyrrolidin-N-yl, 3-carboxamidopiperid-N-yl, 3-hydroxypyrrolidin-N-yl, 4-acetylpiperazin-1-yl, 4-hydroxypiperid-N-yl, 4-methylpiperazin-1-yl, 4-(pyridin-4-yl)piperazin-1-yl, and 2-methoxycarbonylpyrrolidin-N-yl.

Preferred $R^3$ groups include, by way of example, chloro, fluoro and methyl.

In one preferred embodiment, the benzodiazepine ring is disubstituted to provide, for example, dichloro, difluoro and dimethyl substitution.

Most preferably, p is zero (i.e., all of the $R^3$ groups are hydrogen).

Preferred $R^7$ groups include hydrogen, methyl, benzyl, t-butoxycarbonylmethyl and the like.

In a particularly preferred embodiment, Q is —SO$_2$R, W is nitrogen, p is zero (all $R^3$ groups are hydrogen), q is one and $R^2$ and $R^7$ are hydrogen. Such compounds are represented by formula II as follows:

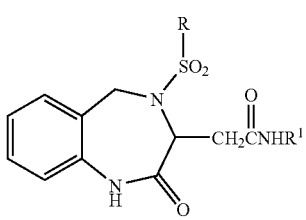

II where R and $R^1$ are as defined above; and pharmaceutically acceptable salts, prodrugs, isomer, and tautomers thereof.

In those cases where the compounds of Formulas I and II exist as optical or geometric isomers, the above formulas are intended to represent isomer mixtures and also the individual BK antagonist. Formulas I and II are also intended to represent the individual isomers as well as mixtures thereof; both of which are encompassed within the scope of this invention.

Compounds within the scope of this invention include those set forth in Tables I and II as follows:

TABLE I (unless indicated otherwise, $R^2$ is hydrogen)

| Comp No. | R | $R^1$ |
|---|---|---|
| 1 | 4-chloro-2,5-dimethylphenyl | 2-(R,S)-[(pyridin-4-yl)]eth-1-yl |
| 2 | 4-chloro-2,5-dimethylphenyl | 2-(R,S)-[1,2,5,6-tetrahydro-N-methylpyridin-4-yl]eth-1-yl |
| 3 | 4-chloro-2,5-dimethylphenyl | 2-(R,S)-[N-methylpiperidin-4-yl)]eth-1-yl |
| 4 | 4-chloro-2,5-dimethylphenyl | 2-(R,S)-[N-(pyridin-4-yl)piperidin-4-yl)]eth-1-yl |
| 5 | 4-chloro-2,5-dimethylphenyl | 2-(R,S)-[N-oxopyridin-4-yl]eth-1-yl |
| 6 | 4-chloro-2,5-dimethylphenyl | $R^1/R^2$ together with the nitrogen attached thereto form 4-(pyridin-2-yl)piperazin-1-yl |

TABLE I-continued (unless indicated otherwise, $R^2$ is hydrogen)

| Comp No. | R | $R^1$ |
|---|---|---|
| 7 | 4-chloro-2,5-dimethylphenyl | $R^1/R^2$ together with the nitrogen attached thereto form 4-(pyridin-4-yl)piperazin-1-yl |
| 8 | 4-chloro-2,5-dimethylphenyl | 2-(R,S)-cyclopropyl-2-(pyridin-4-yl)eth-1-yl |
| 9 | 4-chloro-2,5-dimethylphenyl | 2-(R)-(pyridin-4-yl)eth-1-yl |
| 10 | 4-chloro-2,5-dimethylphenyl | 2-(S)-(pyridin-4-yl)eth-1-yl |
| 11 | 2,3-dichlorophenyl | 2-(R,S)-cyclopropyl-2-(pyridin-4-yl)eth-1-yl |
| 12 | 2,3-dichlorophenyl | 2-(R,S)-(pyridin-4-yl)eth-1-yl |
| 13 | 2,3-dichlorophenyl | 2-(R,S)-[(N-pyridin-2-yl)piperidin-4-yl]eth-1-yl |

TABLE II

| Comp No. | R | $R^1$ |
|---|---|---|
| 14 | 4-chloro-2,5-dimethylphenyl | 2-(R,S)-pyridin-4-yleth-1-yl |

Particularly preferred compounds include the following compounds and pharmaceutically acceptable salts thereof:

3-[3-(R,S)-(4-chloro-2,5-dimethylbenzenesulfonyl)-4-oxo-2,5-benzodiazepin-3-yl]-N-[2-(pyridin-4-yl)ethyl]acetamide (1);

3-[3-(R,S)-(4-chloro-2,5-dimethylbenzenesulfonyl)-4-oxo-2,5-benzodiazepin-3-yl]-N-[2-(1,2,5,6-tetrahydro-N-methylpyridin-4-yl)eth-1-yl]acetamide (2);

3-[3-(R,S)-(4-chloro-2,5-dimethylbenzenesulfonyl)-2-oxo-2,5-benzodiazepin-3-yl]-N-[2-(N-methylpiperidin-4-yl)eth-1-yl]acetamide (3);

3-[3-(R,S)-(4-chloro-2,5-dimethylbenzenesulfonyl)-2-oxo-2,5-benzodiazepin-3-yl]-N-[2-(N-{pyrid-4-yl}piperidin-4-yl)eth-1-yl]acetamide (4);

3-[3-(R,S)-(4-chloro-2,5-dimethylbenzenesulfonyl)-2-oxo-2,5-benzodiazepin-3-yl]-N-[2-(N-oxopyridin-4-yl)eth-1-yl]acetamide (5);

3-[3-(R,S)-(4-chloro-2,5-dimethylbenzenesulfonyl)-2-oxo-2,5-benzodiazepin-3-yl]-N-[4-(pyridin-2-yl)piperazin-1-yl]acetamide (6);

3-[3-(R,S)-(4-chloro-2,5-dimethylbenzenesulfonyl)-2-oxo-2,5-benzodiazepin-3-yl]-N-[4-(pyridin-4-yl)piperazin-1-yl]acetamide (7);

3-[3-(R,S)-(4-chloro-2,5-dimethylbenzenesulfonyl)-2-oxo-2,5-benzodiazepin-3-yl]-N-[2-cyclopropyl-2-(pyridin-4-yl)eth-1-yl]acetamide (8);

3-[3-(R)-(4-chloro-2,5-dimethylbenzenesulfonyl)-4-oxo-2,5-benzodiazepin-3-yl]-N-[2-(pyridin-4-yl)ethyl]acetamide (9);

3-[3-(S)-(4-chloro-2,5-dimethylbenzenesulfonyl)-4-oxo-2,5-benzodiazepin-3-yl]-N-[2-(pyridin-4-yl)ethyl]acetamide (10);

3-[3-(R,S)-(2,3-dichlorobenzenesulfonyl)-2-oxo-2,5-benzodiazepin-3-yl]-N-[2-(R,S)-cyclopropyl-2-(pyridin-4-yl)eth-1-yl]acetamide (11);

3-[3-(R,S)-(2,3-dichlorobenzenesulfonyl)-4-oxo-2,5-benzodiazepin-3-yl]-N-[2-(pyridin-4-yl)ethyl]acetamide (12);

3-[3-(R,S)-(2,3-dichlorobenzenesulfonyl)-2-oxo-2,5-benzodiazepin-3-yl]-N-[2-(N-{pyridin-2-yl}piperidin-4-yl)eth-1-yl]acetamide (13); and 3-[3-(R,S)-(4-chloro-2,5-dimethylphenylcarbonylmethyl)-2-oxo-2,5-benzodiazepin-3-yl]-N-[2-pyridin-4-yleth-1-yl]acetamide (14).

In those cases where the compounds of Formula I and/or II exist as tautomers, optical isomers or geometric isomers, the above formulas are intended to represent each tautomer, isomer mixtures and also the individual isomer BK antagonist or intermediate isomers. Formula I and/or II are intended to represent the individual isomers as well as mixtures thereof; all of which are encompassed within the scope of this invention.

Further, references to the compounds of Formula I and II with respect to pharmaceutical applications thereof are also intended to include pharmaceutically acceptable salts of the compounds of Formula I and II.

The invention also provides methods for determining bradykinin levels in a biological sample which comprises contacting said biological sample with a compound of Formula I, II or mixtures of one or more compounds of Formula I and/or II, at a predetermined concentration.

The present invention also provides a pharmaceutical composition comprising a pharmaceutically acceptable carrier and a therapeutically amount of a compound of Formula I, II or mixtures of one or more compounds of Formula I and/or II effective to treat or palliate adverse symptoms associated with the presence of bradykinin in mammals.

This invention further provides a method for treating or palliating adverse symptoms associated with the presence or secretion of bradykinin in mammals which comprises administering a therapeutically effective amount of a compound Formula I, II or mixtures of one or more compounds of Formula I and/or II or as is more generally the case the pharmaceutical composition.

The present invention provides a method for treating or ameliorating pain, hyperalgesia, hyperthermia and/or edema in mammals associated with the release of bradykinin in such mammals which comprises a therapeutically effective amount of a compound Formula I, II or mixtures of one or more compounds of Formula I and/or II or as is more generally the case the pharmaceutical composition.

The present invention provides a method for treating or ameliorating adverse symptoms associated with the release of bradykinin relative to burns, perioperative pain, migraine, shock, central nervous system injury, asthma, rhinitis, premature labor, inflammatory arthritis, inflammatory bowel disease or neuropathic pain.

DETAILED DESCRIPTION OF THE INVENTION

Definitions and Overview

As discussed above, the present invention is directed to certain sulfonylbenzodiazpinone acetamide derivatives and related compounds.

Before the present invention is described in detail, it is to be understood that unless otherwise indicated this invention is not limited to any particular sulfonylbenzodiazpinone acetamide derivatives, as such may vary. It is also to be understood that the terminology used herein is for the purpose of describing particular embodiments only and is not intended to limit the scope of the present invention. It must be noted that as used herein and in the claims, the singular forms "a," "and" and "the" include plural referents unless the context clearly dictates otherwise. In this specification and in the claims which follow, reference will be made to a number of terms which shall be defined to have the following meanings:

Unless otherwise expressly defined with respect to a specific occurrence of the term, the following terms as used herein shall have the following meanings regardless of whether capitalized or not.

The term benzodiazepinone refers to the ring structure set forth below with the numbering system in the A ring (as employed herein) included therein:

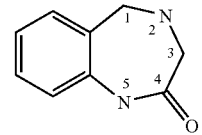

The term "alkyl" refers to alkyl groups having from 1 to 10 carbon atoms and more preferably 1 to 6 carbon atoms and includes both straight chain and branched chain alkyl groups. This term is exemplified by groups such as methyl, t-butyl, n-heptyl, octyl and the like.

The term "substituted alkyl" refers to an alkyl group, of from 1 to 10 carbon atoms, more preferably, 1 to 6 carbon atoms, having from 1 to 5 substituents, preferably 1 to 3 substituents, independently selected from the group consisting of alkoxy, substituted alkoxy, acyl, acylamino, thiocarbonylamino, acyloxy, amino, substituted amino, amidino, alkylamidino, thioamidino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, guanidino, substituted guanidino, guanidinosulfone, thiol, thioalkyl, substituted thioalkyl, thioaryl, substituted thioaryl, thiocycloalkyl, substituted thiocycloalkyl, thioheteroaryl, substituted thioheteroaryl, thioheterocyclic, substituted thioheterocyclic, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{10}$R$^{10}$ where each R$^{10}$ is independently hydrogen or alkyl, —NR$^{10}$S(O)$_2$-alkyl, —NR$^{10}$S(O)$_2$-substituted alkyl, —NR$^{10}$S(O)$_2$-aryl, —NR$^{10}$S(O)$_2$-substituted aryl, —NR$^{10}$S(O)$_2$-heteroaryl, —NR$^{10}$S(O)$_2$-substituted heteroaryl, —NR$^{10}$S(O)$_2$-heterocyclic, —NR$^{10}$S(O)$_2$-substituted heterocyclic, —NR$^{10}$S(O)$_2$—NR$^{10}$-alkyl, —NR$^{10}$S(O)$_2$—NR$^{10}$-substituted alkyl, —NR$^{10}$S(O)$_2$—NR$^{10}$-aryl, —NR$^{10}$S(O)$_2$—NR$^{10}$-substituted aryl, —NR$^{10}$S(O)$_2$—NR$^{10}$-heteroaryl, —NR$^{10}$S(O)$_2$—NR$^{10}$-substituted heteroaryl, —NR$^{10}$S(O)$_2$—NR$^{10}$-heterocyclic, and —NR$^{10}$S(O)$_2$—NR$^{10}$-substituted heterocyclic where each R$^{10}$ is independently hydrogen or alkyl.

"Alkoxy" refers to the group "alkyl-O—" which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Substituted alkoxy" refers to the group "substituted alkyl-O-".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amino" refers to the group —NH$_2$.

"Substituted amino" refers to the group —NR$^{11}$R$^{11}$, where each R$^{11}$ group is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R$^{11}$ groups are not hydrogen; or the R$^{11}$ groups can be joined together with the nitrogen atom to form a heterocyclic or substituted heterocyclic ring.

The "acylamino" or as a prefix "carbamoyl" or "carboxamide" or "substituted carbamoyl" or "substituted carboxamide" refers to the group —C(O)NR$^{12}$R$^{12}$ where each R$^{12}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{12}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Thiocarbonylamino" or as a prefix "thiocarbamoyl", "thiocarboxamido" or "substituted thiocarbamoyl" or "substituted thiocarboxamido" refers to the group —C(S)NR$^{13}$R$^{13}$ where each R$^{13}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic and where each R$^{13}$ is joined to form, together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups acyl-O— where acyl is as defined herein.

"Alkenyl" refers to alkenyl group having from 2 to 10 carbon atoms and more preferably 2 to 6 carbon atoms and having at least 1 and preferably from 1–2 sites of alkenyl unsaturation.

"Substituted alkenyl" refers to alkenyl groups having from 1 to 5 substituents, preferably 1 to 3 substituents, independently selected from the group of substituents defined for substituted alkyl provided that hydroxyl or thiol groups are not substituted to a vinyl or unsaturated carbon atom.

"Alkynyl" refers to alkynyl group having from 2 to 10 carbon atoms and more preferably 3 to 6 carbon atoms and having at least 1 and preferably from 1–2 sites of alkynyl unsaturation.

"Substituted alkynyl" refers to alkynyl groups having from 1 to 5, preferably 1 to 3 substituents, selected from the same group of substituents as defined for substituted alkyl provided that hydroxyl or thiol groups are not substituted to a vinyl or unsaturated carbon atom.

"Amidino" refers to the group H$_2$NC(=NH)— and the term "alkylamidino" refers to compounds having 1 to 3 alkyl groups (e.g., alkylHNC(=NH)—) where alkyl is as defined herein.

"Thioamidino" refers to the group RSC(=NH)— where R is hydrogen or alkyl where alkyl is as defined herein.

"Aminoacyl" refers to the groups —NR$^{14}$C(O)alkyl, —NR$^{14}$C(O)substituted alkyl, —NR$^{14}$C(O)cycloalkyl, —NR$^{14}$C(O)substituted cycloalkyl, —NR$^{14}$C(O)alkenyl, —NR$^{14}$C(O)substituted alkenyl, —NR$^{14}$C(O)alkynyl, —NR$^{14}$C(O)substituted alkynyl, —NR$^{14}$C(O)aryl, —NR$^{14}$C(O)substituted aryl, —NR$^{14}$C(O)heteroaryl, —NR$^{14}$C(O)substituted heteroaryl, —NR$^{14}$C(O)heterocyclic, and —NR$^{14}$C(O)substituted heterocyclic where R$^{14}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

"Aminocarbonyloxy" refers to the groups —NR$^{15}$C(O)O-alkyl, —NR$^{15}$C(O)O-substituted alkyl, —NR$^{15}$C(O)O-alkenyl, —NR$^{15}$C(O)O-substituted alkenyl, —NR$^{15}$C(O)O-alkynyl, —NR$^{15}$C(O)O-substituted alkynyl, —NR$^{15}$C(O)O-cycloalkyl, —NR$^{15}$C(O)O-substituted cycloalkyl, —NR$^{15}$C(O)O-aryl, —NR$^{15}$C(O)O-substituted aryl, —NR$^{15}$C(O)O-heteroaryl, —NR$^{15}$C(O)O-substituted heteroaryl, —NR$^{15}$C(O)O-heterocyclic, and —NR$^{15}$C(O)O-substituted heterocyclic where R$^{15}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxycarbonylamino" or as a prefix "carbamoyloxy" or "substituted carbamoyloxy" refers to the groups —OC(O)NR$^{16}$R$^{16}$ where each R$^{16}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each $R^{16}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxythiocarbonylamino" refers to the groups —OC(S)NR$^{17}$R$^{17}$ where each $R^{17}$ is independently hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic or where each $R^{17}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{18}$C(O)NR$^{19}$R$^{19}$ where $R^{18}$ is selected from the group consisting of hydrogen and alkyl and each $R^{19}$ is independently selected from hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic or where each $R^{19}$ is joined to form together with the nitrogen atom a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{18}$C(S)NR$^{19}$R$^{19}$ where $R^{18}$ is selected from the group consisting of hydrogen and alkyl and each $R^{19}$ is independently selected from hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic or where each $R^{19}$ is joined to form together with the nitrogen atom a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aryl" or "Ar" refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is through an aryl ring atom. Preferred aryls include phenyl and naphthyl.

"Substituted aryl" refers to aryl groups which are substituted with from 1 to 4 substituents, preferably 1 to 3, selected from the group consisting of hydroxy, acyl, acylamino, thiocarbonylamino, acyloxy, alkyl, substituted alkyl, alkoxy, substituted alkoxy, alkenyl, substituted alkenyl, alkynyl, substituted alkynyl, amidino, alkylamidino, thioamidino, amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocylyloxy, carboxyl, carboxyl esters, cyano, thiol, thioalkyl, substituted thioalkyl, thioaryl, substituted thioaryl, thioheteroaryl, substituted thioheteroaryl, thiocycloalkyl, substituted thiocycloalkyl, thioheterocyclic, substituted thioheterocyclic, cycloalkyl, substituted cycloalkyl, guanidino, substituted guanidino, guanidinosulfone, halo, nitro, heteroaryl, substituted heteroaryl, heterocyclic, substituted heterocyclic, oxycarbonylamino, oxythiocarbonylamino, —S(O)$_2$-alkyl, —S(O)$_2$-substituted alkyl, —S(O)$_2$-cycloalkyl, —S(O)$_2$-substituted cycloalkyl, —S(O)$_2$-alkenyl, —S(O)$_2$-substituted alkenyl, —S(O)$_2$-aryl, —S(O)$_2$-substituted aryl, —S(O)$_2$-heteroaryl, —S(O)$_2$-substituted heteroaryl, —S(O)$_2$-heterocyclic, —S(O)$_2$-substituted heterocyclic, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, —OSO$_2$—NR$^{20}$R$^{20}$ where each $R^{20}$ is independently hydrogen or alkyl, —NR$^{21}$S(O)$_2$-alkyl, —NR$^{21}$S(O)$_2$-substituted alkyl, —NR$^{21}$S(O)$_2$-aryl, —NR$^{21}$S(O)$_2$-substituted aryl, —NR$^{21}$S(O)$_2$-heteroaryl, —NR$^{21}$S(O)$_2$-substituted heteroaryl, —NR$^{21}$S(O)$_2$-heterocyclic, —NR$^{21}$S(O)$_2$-substitute heterocyclic, —NR$^{21}$S(O)$_2$—NR$^{21}$-alkyl, —NR$^{21}$S(O)$_2$—NR$^{21}$-substituted alkyl, —NR$^{21}$S(O)$_2$—NR$^{21}$-aryl, —NR$^{21}$S(O)$_2$—NR-substituted aryl, —NR$^{21}$S(O)$_2$—NR$^{21}$-heteroaryl, —NR$^{21}$S(O)$_2$—NR$^{21}$-substituted heteroaryl, —NR$^{21}$S(O)$_2$—NR$^{21}$-heterocyclic, —NR$^{21}$S(O)$_2$—NR$^{21}$-substituted heterocyclic where each $R^{21}$ is independently hydrogen or alkyl, wherein each of the terms is as defined herein.

"Aryloxy" refers to the group aryl-O— which includes, by way of example, phenoxy, naphthoxy, and the like wherein aryl is as defined herein.

"Substituted aryloxy" refers to substituted aryl-O— groups where substituted aryl is as defined herein.

"Aryloxyaryl" refers to the group -aryl-O-aryl where aryl is as defined herein.

"Substituted aryloxyaryl" refers to aryloxyaryl groups substituted with from 1 to 4 substituents, preferably 1 to 3 substituents on either or both aryl rings independently selected from the same group consisting of substituents as defined for substituted aryl.

"Carboxyl" or "carboxy" refers to the group —COOH and pharmaceutically acceptable salts thereof.

"Carboxyl esters" refers to the groups —COO-alkyl, —COO-substituted alkyl, —COO-cycloalkyl, —COO-substituted cycloalkyl, —COO-aryl, —COO-substituted aryl, —COO-hetereoaryl, —COO-substituted heteroaryl, —COO-hetereocyclic, and —COO-substituted heterocyclic wherein each of alkyl, substituted alkyl, cycloalkyl, substituted cycloalkyl, aryl, substituted aryl, heteroaryl, substituted heteroaryl, heterocyclic and substituted heterocyclic are as defined herein.

"Cycloalkyl" refers to cyclic alkyl groups of from 3 to 10 carbon atoms having a single or multiple cyclic rings including, by way of example, cyclopropyl, cyclobutyl, cyclopentyl, cyclooctyl, adamantanyl, and the like.

"Cycloalkenyl" refers to cyclic alkenyl groups of from 3 to 8 carbon atoms having single or multiple unsaturation but which are not aromatic.

"Substituted cycloalkyl" and "substituted cycloalkenyl" refer to cycloalkyl and cycloalkenyl groups, as defined herein, having from 1 to 5, preferably 1 to 3 substituents independently selected from the same group of substituents as defined for substituted alkyl.

"Cycloalkoxy" refers to —O-cycloalkyl groups where cycloalkyl is as defined herein.

"Substituted cycloalkoxy" refers to —O-substituted cycloalkyl groups where substituted cycloalkyl is as defined herein.

"Guanidino" or "substituted guanidino" refers to the groups —NR$^{22}$C(=NR$^{22}$)NR$^{23}$R$^{23}$ where each R$^{22}$ is independently hydrogen or alkyl and each R$^{23}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Guanidinosulfone" refers to the groups —NR$^{22}$C(=NR$^{22}$)NR$^{22}$SO$_2$-alkyl, —NR$^{22}$C(=NR$^{22}$)NR$^{22}$SO$_2$-substituted alkyl, —NR$^{22}$C(=NR$^{22}$)NR$^{22}$SO$_2$-alkenyl, —NR$^{22}$C(=NR$^{22}$)NR$^{22}$SO$^2$-substituted alkenyl, —NR$^{22}$C(=NR$^{22}$)NR$^{22}$SO$_2$-alkynyl, —NR$^{22}$C(=NR$^{22}$)NR$^{22}$SO$_2$-substituted alkynyl, —NR$^{22}$C(=NR$^{22}$)NR$^{22}$SO$_2$-aryl, —NR$^{22}$C(=NR$^{22}$)NR$^{22}$SO$_2$-substituted aryl, —NR$^{22}$C(=NR$^{22}$)NR$^{22}$SO$_2$-cycloalkyl, —NR$^{22}$C(=NR$^{22}$)NR$^{22}$SO$_2$-substituted cycloalkyl, —NR$^{22}$C(=NR$^{22}$)NR$^{22}$SO$_2$-heteroaryl, —NR$^{22}$C(=NR$^{22}$)NR$^{22}$SO$_2$-substituted heteroaryl, —NR$^{22}$C(=NR$^{22}$)NR$^{22}$SO$_2$-heterocyclic, and —NR$^{22}$C(=NR$^{22}$)NR$^{22}$SO$_2$-substituted heterocyclic where each R' is independently hydrogen and alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Halo" or "halogen" refers to fluoro, chloro, bromo and iodo and preferably is either chloro or fluoro.

"Heteroaryl" refers to an aromatic group of from 1 to 10 ring carbon atoms and 1 to 4 ring heteroatoms selected from oxygen, nitrogen and sulfur within the ring. Such heteroaryl groups can have a single ring (e.g., pyridyl or furyl) or multiple condensed rings (e.g., indolizinyl or benzothienyl) wherein the condensed ring may or may not be heteroaryl, e.g., cycloalkyl, heterocyclic or aryl rings, provided that the point of attachment is through a heteroaryl ring atom. Preferred heteroaryls include pyridyl, pyrrolyl, indolyl and furyl.

"Substituted heteroaryl" refers to heteroaryl groups, as defined above, which are substituted with from 1 to 3 substituents independently selected from the same group of substituents as defined for "substituted aryl". Also included within the term "substituted heteroaryl" for nitrogen-containing heteroaryls are N-oxides.

"Heteroaryloxy" refers to the group —O-heteroaryl and "substituted heteroaryloxy" refers to the group —O-substituted heteroaryl where heteroaryl and substituted heteroaryl are as defined above.

"Heterocycle" or "heterocyclic" refers to a saturated or unsaturated group having a single ring or multiple condensed rings, from 1 to 10 ring carbon atoms and from 1 to 4 ring hetero atoms selected from nitrogen, sulfur or oxygen within the ring wherein, in fused ring systems, one or more of the rings can be cycloalkyl, aryl or heteroaryl provided that the point of attachment is through a heterocyclic ring atom.

"Saturated heterocyclic" refers to heterocycles of single or multiple condensed rings lacking unsaturation in any ring (e.g., carbon to carbon unsaturation, carbon to nitrogen unsaturation, nitrogen to nitrogen unsaturation, and the like).

"Unsaturated heterocyclic" refers to non-aromatic heterocycles of single or multiple condensed rings having unsaturation in any ring (e.g., carbon to carbon unsaturation, carbon to nitrogen unsaturation, nitrogen to nitrogen unsaturation, and the like).

"Substituted heterocyclic" refers to heterocycle groups, as defined above, which are substituted with from 1 to 3 substituents independently selected from the group consisting of oxo (=O), thioxo (=S), plus the same group of substituents as defined for substituted aryl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholino, thiomorpholino, piperidinyl, pyrrolidine, tetrahydrofuranyl, and the like.

"Substituted saturated heterocyclic" refers to substituted heterocycles, as defined above, of single or multiple condensed rings lacking unsaturation in any ring (e.g., carbon to carbon unsaturation, carbon to nitrogen unsaturation, nitrogen to nitrogen unsaturation, and the like).

"Substituted unsaturated heterocyclic" refers to non-aromatic substituted heterocycles of single or multiple condensed rings having unsaturation in any ring (e.g., carbon to carbon unsaturation, carbon to nitrogen unsaturation, nitrogen to nitrogen unsaturation, and the like).

"Heterocyclyloxy" refers to the group —O-heterocyclic and "substituted heterocyclyloxy" refers to the group —O-substituted heterocyclic where heterocyclic and substituted heterocyclyoxy are as defined above.

"Thiol" refers to the group —SH.

"Thioalkyl" refers to the groups —S-alkyl where alkyl is as defined above.

"Substituted thioalkyl" refers to the group —S-substituted alkyl where substituted alkyl is as defined above.

"Thiocycloalkyl" refers to the groups —S-cycloalkyl where cycloalkyl is as defined above.

"Substituted thiocycloalkyl" refers to the group —S-substituted cycloalkyl where substituted cycloalkyl is as defined above.

"Thioaryl" refers to the group —S-aryl and "substituted thioaryl" refers to the group —S-substituted aryl where aryl and substituted aryl are as defined above.

"Thioheteroaryl" refers to the group —S-heteroaryl and "substituted thioheteroaryl" refers to the group —S-substituted heteroaryl where heteroaryl and substituted heteroaryl are as defined above.

"Thioheterocyclic" refers to the group —S-heterocyclic and "substituted thioheterocyclic" refers to the group —S-substituted heterocyclic where heterocyclic and substituted heterocyclic are as defined above.

"Pharmaceutically acceptable salt" refers to pharmaceutically acceptable salts of a compound of Formula I and/or II which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Prodrugs" as used herein, are compounds which convert (e.g., hydrolyze, metabolize) in vivo to a compound of the invention. The effectiveness of an orally administered drug is dependent upon the drug's efficient transport across the mucosal epithelium and its stability in enterohepatic circulation. Drugs that are effective after parenteral administration but less effective orally, or whose plasma half-life is considered too short, may be chemically modified into a prodrug form. The prodrug should have a pharmacokinetic profile that is different from that of the parent, enabling easier absorption across the mucosal epithelium, better salt formulation and/or solubility, and/or improved systemic stability (for an increase in plasma half-life, for example). Many chemical modifications may be suitable for the creation of the prodrugs according to the invention, including:
(1) Ester or amide derivatives which may be cleaved by, for example, esterases or lipases. For ester derivatives, the ester is derived from the carboxylic acid moiety of the drug molecule by known means. For amide derivatives, the amide may be derived from the carboxylic acid moiety or the amine moiety of the drug molecule by known means.
(2) Peptides that may be recognized by specific or nonspecific proteinases. A peptide may be coupled to the drug molecule via amide bond formation with the amine of carboxylic acid moiety of ht drug molecule by known means.
(3) Derivatives that accumulate at a site of action through membrane selection of a prodrug form or modified prodrug form.
(4) Any combination of (1) to (3).

It will further be appreciated by those skilled in the art that certain moieties known to those skilled in the art as "promoieties", for example as described in "Design of Prodrugs" by Bundgaard (Elsevier) 1985, may be placed on appropriate functionalities when such functionalities are present in compounds of the invention also to form a prodrug. Further, certain compounds of the invention may act as prodrugs of other compounds of the invention. All protected derivatives, and prodrugs, of the compounds of the invention are included within the scope of the invention.

As used with any of the defined terms, the word "substituted" as used with, for example, "substituted alkyl" does not and is not intended to include polymers derived therefrom but are limited to a maximum of 3 substituents groups, e.g., Ar—Ar—Ar.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in Greene and Wuts, Protecting Groups in Organic Synthesis, Second Edition, Wiley, N.Y., 1991, and references cited therein.

The compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

Specifically, the sulfonylbenzodiazepinone acetamide derivatives and related compounds (Q=—SO$_2$R) are preferably prepared as shown in Scheme (1) below:

SCHEME 1

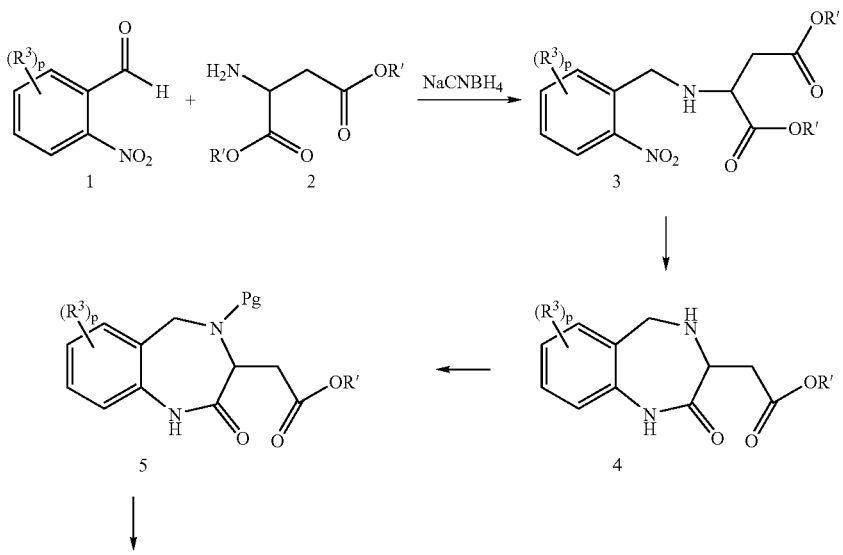

-continued

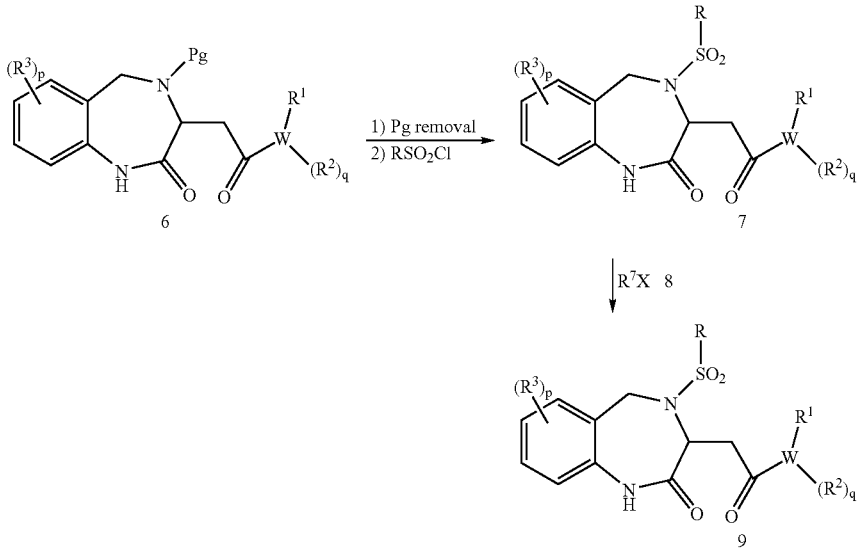

where R, $R^1$, $R^2$, $R^3$, $R^7$, W, p and q are as defined above and each R' is independently alkyl or substituted alkyl.

Specifically, as shown in Scheme 1, an appropriately substituted 2-nitrobenzaldehyde compound, 1, is combined with at least an equivalent of an aspartic acid diester, 2, in the presence of a suitable reducing agent such as sodium cyanoborohydride under conventional reductive amination conditions to provide for the optionally substituted N-(2-nitrobenzyl)aspartic acid diester, 3. The reaction is typically conducted in an inert solvent such as methanol or ethanol at a temperature of from about 0° C. to about 60° C., although preferably at room temperature. The reaction is continued until substantial completion which typically occurs within about 1 to 24 hours. The resulting product can be recovered by conventional methods, such as solvent stripping, chromatography, filtration, crystallization, and the like, or can be used in the next step without purification and/or isolation.

Reduction of the nitro group of the optionally substituted N-(2-nitrobenzyl) aspartic acid diester, 3, with concomitant ring closure provides for the benzodiazepinone derivative, 4, as shown in reaction scheme (1). Specifically, reduction of the nitro group to the intermediate amino group is accomplished under catalytic reduction conditions in the presence of elevated pressures of hydrogen. The reaction is typically conducted at a temperature of from about 0° C. to about 60° C., although preferably at room temperature and is continued until substantial completion which typically occurs in about 0.5 to 12 hours. The resulting amine is preferably reacted with at least an equivalent of trimethyl aluminum in a suitable solvent such as toluene or benzene at a temperature of from about −20° C. to about 25° C. although preferably by starting at 0° C. and warming the reaction to room temperature over a period of about 0.5 to about 6 hours or until substantially complete. The resulting product can be recovered by conventional methods, such as solvent stripping, chromatography, filtration, crystallization, and the like, or can be used in the next step without purification and/or isolation.

The 2-amino group of benzodiazepinone derivative, 4, is then protected with a conventional protecting group (Pg), e.g., t-Boc, under conventional conditions that well known in the art, to provide for the N-protected benzodiazepinone derivative, 5.

Compounds of Formula I (where W is N) can be prepared by first hydrolyzing the ester of the N-protected benzodiazepinone derivative, 5, and then reacting the resulting carboxyl group of compound 5a with a slight excess of a primary or secondary amine or nitrogen heterocycle, $HNR^1R^2$, followed by removal of the protecting group, Pg, as shown in Scheme 2 below:

Scheme 2

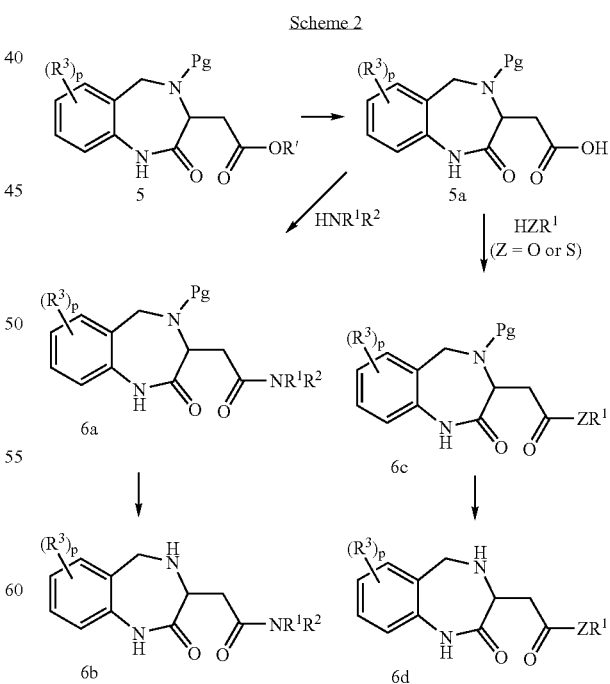

where R', $R^1$, $R^2$, $R^3$, p and Pg are as defined above and Z is oxygen or sulfur.

The reaction is preferably in the presence of an inert organic solvent, a coupling agent and an organic base using amidation methods well known in the art. This reaction is preferably conducted using an approximate equivalent to a slight excess of an amine (HNR$^1$R$^2$) (about from 0.99 to 1.2 molar equivalents per mole of N-protected benzodiazepinone, 5a) at temperatures in the range of about −20° C. to room temperature. The reaction is continued until substantial completion, which typically occurs in 2 to 12 hours. Suitable inert organic solvents which can be used include, for example, N,N-dimethylformamide, acetonitrile, dichloromethane, and the like. Suitable coupling agents which may be used include 1-hydroxybenzotriazole hydrate (HOBT) and 1-(3-dimethyl-aminopropyl)-3-ethylcarbodiimide hydrochloride (EDCI), diphenylphosphoryl azide (DPPA), and the like. Suitable organic bases include triethylamine (TEA), pyridine, N-methyl morpholine, diisopropylethyl amine (DIEA) and the like. The resulting product can be recovered by conventional methods, such as solvent stripping, chromatography, filtration, crystallization, and the like, or can be used in the next step without purification and/or isolation.

For compounds of Formula I wherein W is O or S, the carboxyl group of the N-protected benzodiazepinone, 5a, is esterified or thioesterified by contacting this intermediate with an appropriate alcohol or thiol (HZR$^1$ wherein Z is O or S). The esterification reaction may be catalyzed by H$^+$. The thioesterification is typically performed in an inert organic solvent, for example, pyridine, and is typically conducted with a stoichiometric amount of a dehydration agent, chlorinating agent, or activating agent, such as POCl$_3$. The reaction is typically conducted at temperatures in the range of −20° C. to −10° C. until reaction completion, which typically occurs in 1 to 3 hours. The resulting product, compound 6c, can be recovered by conventional methods, such as solvent stripping, chromatography, filtration, crystallization, and the like, or can be used in the next step without purification and/or isolation.

Whether W is N, S or O, the protecting group on compound 6 (Scheme 1) or on compounds 6a and 6c (Scheme 2) is then removed under conditions well known in the art to provide for the free amine [compounds 6b and 6d (Scheme 2)] followed by sulfonation with the desired sulfonyl chloride RSO$_2$Cl, to yield the sulfonylbenzodiazepinone acetamide, sulfonylbenzodiazepinone acetic acid ester, or thioester, compound 7 (Q=—SO$_2$R). The sulfonation reaction is typically effected by contacting the deprotected benzodiazepinone intermediate with about a stoichiometric amount, or slight excess, of the desired sulfonyl chloride in the presence of a scavenger base, such as pyridine, and the like in an inert diluent. The reaction is typically conducted at temperatures in the range of about 0° C. to about room temperature for a period of time to effect sulfonation, which is typically 2 to 12 hours. Suitable inert solvents which can be used include, dichloromethane, and the like. The resulting product can be recovered by conventional methods, such as chromatography, filtration, crystallization, and the like, or can be used in the next step without purification or isolation.

The preparation of compounds of Formula I where R$^7$ is other than hydrogen can be accomplished in several methods, two of which are illustrated herein. For R$^7$ groups such as alkyl or substituted alkyl, the sulfonylbenzodiazepinone acetamide, sulfonylbenzodiazepinone acetic acid ester, or thioester, compound 7 is contacted with about a stoichiometric amount, or slight excess, of the desired R$^7$ halide, compound 8, in the presence of a suitable base, such as sodium carbonate, cesium carbonate, potassium carbonate, and the like in an inert diluent such as DMF, THF and the like. The reaction is typically conducted at temperatures from about 20° C. to about 80° C. for a period of time sufficient for reaction completion, which is typically 2 to 12 hours. The resulting product, compound 9, can be recovered by conventional methods, such as chromatography, filtration, crystallization, and the like.

Alternatively, formation of an R$^7$ substituted sulfonylbenzodiazepinone acetamide, sulfonylbenzodiazepinone acetic acid ester, or thioester, compound 9, can be achieved from use of appropriate starting materials such as an appropriately amino substituted and optionally amino protected 2-aminobenzaldehyde 15. This compound can be employed in place of the o-nitrobenzaldehyde, compound 1, in Scheme 1 with the exception that reduction of the nitro group as depicted therein is replaced by conventional removal of the blocking group when employed. It is understood, of course, that in such a synthetic scheme, the R$^7$ group is limited to those substituents which permit ring cyclization to form the R$^7$ substituted benzodiazepinone compounds.

The synthesis of compound 15 is illustrated in Scheme 3 below:

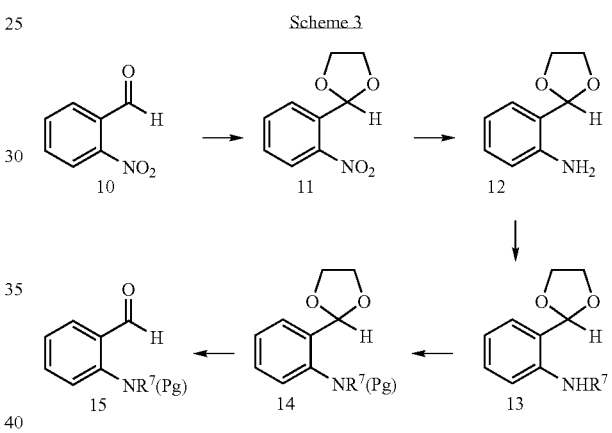

Scheme 3

Specifically, commercially available 2-nitrobenzaldehyde, 10, is carbonyl-protected by conventional formation of ketal 11. Subsequent reduction of the nitro group to the amino group in the manner described above provides for compound 12 which, in turn, is N-substituted in a conventional manner to provide for compound 13. If necessary, the NH group of compound 13 is protected with a conventional protecting group such as a Cbz or a t-Boc group to form compound 14. This compound is then deprotected to regenerate the carbonyl group under conventional conditions to provide for compound 15.

Compound 15 is then combined with at least an equivalent of an aspartic acid diester, 2, in the presence of a suitable reducing agent such as sodium cyanoborohydride under conventional reductive amination conditions to provide for the N-(2-NR$^7$(Pg)benzyl) aspartic acid diester. Subsequent removal of the protecting group, ring closure as described above and optional derivatization as also described above provides for compounds of Formula I.

Compounds of Formula I where Q is —CH$_2$C(O)R are readily prepared in the manner described above except that a suitable α-haloarylacetyl compound, α-haloheteroarylacetyl compound, or α-haloheterocyclylacetyl compound, X—CH$_2$C(O)R, where X is chloro or bromo and R is as defined herein, is used in place of the sulfonyl halide in Scheme 1. The halide reacts with the free amine under conventional conditions well known in the art to provide for the corresponding —CH$_2$C(O)R substitution for the Q group. This compound can then be derivatized as described in Scheme 1 above to provide for compounds of Formula I where Q is a —CH$_2$C(O)R group. Examples of suitable halides include those where R is an optionally substituted phenyl group, an optionally substituted naphthyl group, an optionally substituted heteroaryl group, and the like.

The starting materials for the above reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1–15 (John Wiley and Sons, 1991), Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4th Edition), and Larock's Comprehensive Organic Transformations (VCH Publishers Inc., 1989).

Sulfonyl chlorides of the formula RSO$_2$Cl as employed in the above reaction are either known compounds or compounds that can be prepared from known compounds by conventional synthetic procedures. Such compounds are typically prepared from the corresponding sulfonic acid, i.e., from compounds of the formula R—SO$_3$H where R is as defined above, using phosphorous trichloride and phosphorous pentachloride. This reaction is generally conducted by contacting the sulfonic acid with about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours to afford the sulfonyl chloride. Alternatively, the sulfonyl chlorides can be prepared from the corresponding thiol compound, i.e., from compounds of the formula R—SH where R is as defined herein, by treating the thiol with chlorine (Cl$_2$) and water under conventional reaction conditions.

Examples of sulfonyl chlorides suitable for use in this invention include, but are not limited to, benzenesulfonyl chloride, 1-naphthalenesulfonyl chloride, 2-naphthalenesulfonyl chloride, p-toluenesulfonyl chloride, α-toluenesulfonyl chloride, 4-acetamidobenzenesulfonyl chloride, 4-amidinobenzenesulfonyl chloride, 4-tert-butylbenzenesulfonyl chloride, 4-bromobenzenesulfonyl chloride, 2-carboxybenzenesulfonyl chloride, 4-cyanobenzenesulfonyl chloride, 3,4-dichlorobenzenesulfonyl chloride, 3,5-dichlorobenzenesulfonyl chloride, 3,4-dimethoxybenzenesulfonyl chloride, 3,5-ditrifluoromethylbenzenesulfonyl chloride, 4-fluorobenzenesulfonyl chloride, 4-methoxybenzenesulfonyl chloride, 2-methoxycarbonylbenzenesulfonyl chloride, 4-methylamidobenzenesulfonyl chloride, 4-nitrobenzenesulfonyl chloride, 4-thioamidobenzenesulfonyl chloride, 4-trifluoromethylbenzenesulfonyl chloride, 4-trifluoromethoxybenzenesulfonyl chloride, 2,4,6-trimethylbenzenesulfonyl chloride, 2-phenylethanesulfonyl chloride, 2-thiophenesulfonyl chloride, 5-chloro-2-thiophenesulfonyl chloride, 2,5-dichloro-4-thiophenesulfonyl chloride, 2-thiazolesulfonyl chloride, 2-methyl-4-thiazolesulfonyl chloride, 1-methyl-4-imidazolesulfonyl chloride, 1-methyl-4-pyrazolesulfonyl chloride, 5-chloro-1,3-dimethyl-4-pyrazolesulfonyl chloride, 3-pyridinesulfonyl chloride, 2-pyrimidinesulfonyl chloride and the like. If desired, a sulfonyl fluoride, sulfonyl bromide or sulfonic acid anhydride may be used in place of the sulfonyl chloride in the above reactions.

The synthesis of α-haloacetyl substituted aromatic, heteroaromatic and heterocyclic compounds, including those optionally substituted with one to three R$^3$ groups is well known in the art and documented in numerous basic organic chemistry texts. Numerous such compounds are also commercially available including 2-bromoacetophenone, 2,4'-dichloroacetophenone, 2,2',4'-trichloro-acetophenone, 2,3',4'-trichloroacetophenone, 2-chloro-2',4'-difluoroacetophenone, 2-bromo-4'-methylacetophenone, and the like. Formation of the 2-chloro(4-chloro-2,5-dimethylphenyl)acetophenone is given in Example 2 below.

Optionally substituted α-nitrobenzaldehyde compounds of the formula:

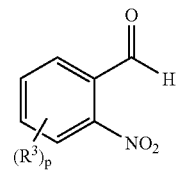

are either commercially available or can be prepared by conventional methods such as conventional halogenation reactions on the phenyl ring, carboxylation reactions on the phenyl ring, etc. If necessary, the carbonyl group of the aldehyde can be first protected by conversion, for example, to a ketal group followed by reaction on the phenyl group. After completion of the desired substitution on the phenyl ring, the ketal group can be removed by conventional procedures.

Similarly, amines of the formula HNR$^1$R$^2$ are either commercially available or can be prepared by methods well known in the art.

In some cases it may be more convenient to prepare a given product compound or intermediate by preparing it from another product of Formula I or intermediate, by applying known synthesis procedures. For example, as noted above, conversion of R$^7$=hydrogen compounds into other R$^7$ moieties can be accomplished after formation of compounds within the scope of Formula I above.

Pharmaceutical Formulations

When employed as pharmaceuticals, the compounds of Formula I and II are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I and II above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity mg/capsules |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity mg/capsules |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity mg/capsules |
|---|---|
| Active Ingredient | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

FORMULATION EXAMPLE 5

Capsules, each containing 40 mg of medicament are made as follows:

| Ingredient | Quantity mg/capsules |
|---|---|
| Active Ingredient | 40.0 |
| Starch | 109.0 |
| Magnesium stearate | 1.0 |
| Total | 150.0 |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount (mg) |
|---|---|
| Active Ingredient | 25 |
| Saturated fatty acid glycerides | 2,000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity mg/capsules |
|---|---|
| Active Ingredient | 15.0 |
| Starch | 407.0 |
| Magnesium stearate | 3.0 |
| Total | 425.00 |

The active ingredient, cellulose, starch, and magnesium stearate are blended, passed through a No. 20 mesh U.S. sieve, and filled into hard gelatin capsules in 560 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 mL |

A topical formulation may be prepared as follows:

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, which is incorporated herein by reference in its entirety. Such patches may be constructed for continuous, palatial, or on demand delivery of pharmaceutical agents.

When it is desirable or necessary to introduce the pharmaceutical composition to the brain, either direct or indirect techniques may be employed. Direct techniques usually involve placement of a drug delivery catheter into the host's ventricular system to bypass the blood-brain barrier. One such implant able delivery system used for the transport of biological factors to specific anatomical regions of the body is described in U.S. Pat. No. 5,011,472 which is incorporated herein by reference in its entirety.

Indirect techniques, which are generally preferred, usually involve formulating the compositions to provide for drug lamentation by the conversion of hydrophilic drugs into lipid-soluble drugs. Lamentation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypersonic solutions which can transiently open the blood-brain barrier.

Utility

The compounds of this invention are bradykinin antagonists and therefore are suitable for use in blocking or ameliorating pain as well as hyperalgesia in mammals. Pain blocked or ameliorated by the compounds of this invention include, for example, pain associated with surgical procedures, burns, trauma, migraine, and the like.

The compounds of this invention are also useful in the treatment of disease conditions in a mammal which are mediated at least in part by bradykinin. Examples of such disease conditions include asthma, rhinitis, premature labor, inflammatory arthritis, inflammatory bowel disease, endotoxic shock related to bacterial infections, central nervous system injury, back pain, neuropathic pain, spinal cord injury and the like.

As noted above, the compounds of this invention are typically administered to the mammal in the form of a pharmaceutical composition. Pharmaceutical compositions of the invention are suitable for use in a variety of drug delivery systems. Suitable formulations for use in the present invention are found in Remington's Pharmaceutical Sciences, Mace Publishing Company, Philadelphia, Pa., 17th ed. (1985). In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like all of which are within the skill of the attending clinician. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

In addition to the above, the esters and thioesters of formula I are useful intermediates in the preparation of the amides of formula I (W=N).

The following synthetic and biological examples are offered to illustrate this invention and are not to be construed in any way as limiting the scope of this invention.

EXAMPLES

Unless otherwise stated all temperatures are in degrees Celsius. Also, in these examples and elsewhere, abbreviations have the following meanings:

| | |
|---|---|
| Boc = | t-butoxycarbonyl |
| brd = | broad doublet |
| brm = | broad multiplet |
| brt = | broad triplet |
| bs = | broad singlet |
| dba = | dibenzyledene acetone |
| dd = | doublet of doublets |
| DIAD = | diisopropyl azo dicarboxylate |
| DIEA = | diisopropylethyl amine |
| DMAP = | 4-N,N-dimethylaminopyridine |
| DME = | dimethoxyethane |
| DMF = | N,N-dimethylformamide |
| DPPA = | diphenylphosphoryl azide |
| dppf = | 1,1-bis(diphenylphosphino)ferrocene |
| dt = | doublet of triplets |
| EDCI = | 1-(3-dimethylaminopropyl)-3-ethylcarbodiimide hydrochloride |
| EtOH = | ethanol |
| eq. = | equivalents |
| g = | gram |
| h = | hours |
| HOAc = | acetic acid |
| HOBT = | 1-hydroxybenzothiazole hydrate |
| HPLC = | high performance liquid chromatography |
| MS = | mass spectroscopy |
| MeOH = | methanol |
| m = | multiplet |
| M = | molar |
| mg = | milligram |
| min. = | minutes |
| mL = | milliliter |
| mmol = | millimolar |
| NMR = | nuclear magnetic resonance |
| N = | normal |
| OAc = | acetate |
| psi = | pounds per square inch |
| q = | quartet |
| rt = | room temperature |
| $R_t$ = | retention time |
| s = | singlet |
| t = | triplet |
| TEA = | triethylamine |
| TFA = | trifluoroacetic acid |
| THF = | tetrahydrofuran |
| μL = | microliters |
| $AsPh_3$ = | triphenyl arsenic |

In the following examples and procedures, the term "Aldrich" indicates that the compound or reagent used in the procedure is commercially available from Aldrich Chemical Company, Inc., Milwaukee, Wis. 53233 USA; the term "Sigma" indicates that the compound or reagent is commercially available from Sigma, St. Louis Mo. 63178 USA and the term "TCI" indicates that the compound or reagent is commercially available from TCI America, Portland Oreg. 97203; the term "Frontier" or "Frontier Scientific" indicates that the compound or reagent is commercially available from Frontier Scientific, Utah, USA; "Bachem" indicates that the compound or reagent is commercially available from Bachem, Torrance, Calif., USA. The following general procedures illustrate general synthetic pathways for preparing amine intermediates useful in preparing compounds of Formula I or for modifying the acetamide group on compounds of formula I.

General Procedure A

General Procedure for the Preparation of 1,2,5,6-Tetrahydro-N-alkylpyridine Derivatives A suitable starting material comprising a 2-acetamide group on a 3-[3-(R,S)-2-arylsulfonyl-4-oxo-2,5-benzodiazepin-3-yl]acetamide compound having a pyridine functionality attached thereto (2.92 mmol) is added to dry DMF (15 mL) and is heated with a heat-gun (if required) to form a clear solution which is then cooled to rt. Methyl iodide (5 mL, excess) is added thereto and stirring is continued for 18 h at rt. Excess DMF is removed under reduced pressure and the pyridinium salt formed is taken to the next step without further purification. The methyl iodide salt is dissolved in methanol (25 mL) and $NaBH_4$ (13.78 mmol) is added to it and stirred for 1 h. Excess MeOH is removed and water (50 mL) is added to the crude product and sonicated for 10 min. A solid product containing the 1,2,5,6-tetrahydro-N-methylpyridine group is filtered off or extracted with $CH_2Cl_2$ and used in the next step without further purification.

The remaining double bond in the 1,2,5,6-tetrahydro-N-methylpyridine group can optionally be hydrogenated to provide for the N-methylpiperidin-4-yl derivative.

General Procedure B

General Procedure for the Preparation of Cyclopropylpiperidinylethyl Acetamides

3-[3-(R,S)-2-(4-chloro-2,5-dimethylbenzenesulfonyl)-4-oxo-2,5-benzodiazepin-3-yl]-N-[2-(pyrid-4-yl)eth-1-yl]acetamide, which can be prepared by amidation of the corresponding carboxylic acid with 2-(2-aminoethyl)pyridine (TCI) in the manner described above is hydrogenated in the presence of platinum oxide ($PtO_2$) in methanol to provide for 3-[3-(R,S)-2-(4-chloro-2,5-dimethylbenzenesulfonyl)-4-oxo-2,5-benzodiazepin-3-yl]-N-[2-(piperidin-4-yl)eth-1-yl] acetamide. Sodium cyanoborohydride (1.5 mmol) is added to a stirred solution of 3-[3-(R,S)-2-(4-chloro-2,5-dimethylbenzenesulfonyl)-4-oxo-2,5-benzodiazepin-3-yl]-N-[2-(piperidin-4-yl)eth-1-yl]acetamide (1 mmol), with 1-ethoxy-1-trimethylsiloxy cyclopropane (1 mmol) (Aldrich) and AcOH (1 mmol) in MeOH (20 mL) at rt. After being stirred at rt, the reaction mixture is refluxed for 18 h. The excess solvent is removed and washed with saturated $NaHCO_3$ solution. The aqueous solution is extracted with $CH_2Cl_2$ (2×100 mL). The combined organic layers are dried and concentrated. The resulting residue is then purified by silica gel column chromatography to afford the N-cyclopropylpiperidinylethyl acetamide derivative.

General Procedure C

General Procedure for the Preparation of N-Phenylpiperidinylethyl Acetamides

Triphenylbismuth diacetate ($Ph_3Bi(OAc)_2$) (1.2 eq.) and $Cu(OAc)_2$ (0.12 eq.) are added to a stirred solution of 3-[3-(R,S)-2-(4-chloro-2,5-dimethyl-benzenesulfonyl)-4-oxo-2,5-benzodiazepin-3-yl]-N-[2-(piperidin-4-yl)eth-1-yl] acetamide (1 mmol) in dichloromethane at rt and stirred for 18 h. The reaction mixture is partitioned between dichloromethane (50 mL) and water (50 mL) and stirred for 2 h. The organic layer is separated, dried and concentrated. The residue was chromatographed on silica gel affording the N-[2-(N-phenyl-piperidin-4-yl)eth-1-yl]acetamide derivative.

General Procedure D

General Procedure for the Preparation of N-Pyridylpiperidinylethyl Acetamides

A solution of 3-[3-(R,S)-2-(4-chloro-2,5-dimethylbenzenesulfonyl)-4-oxo-2,5-benzodiazepin-3-yl]-N-[2-(piperidin-4-yl)eth-1-yl]acetamide (0.1 mmol) and 4-chloropyridine (excess) in EtOH (5 mL) is heated in a sealed tube at 110° C. for 16 h. Excess solvent is removed and the residue purified by preparative HPLC (acetonitrile-water-0.1% TFA) and the N-[2-({N-pyrid-4-yl}piperidin-4-yl)eth-1-yl] acetamide derivative is isolated as the TFA salt.

General Procedure E

General Procedure for Removal of Boc Protecting Groups from Amino Groups

To a stirred solution of Boc-amine (0.01 mol) in dry ethyl acetate (25 mL) at 0° C., HCl gas is bubbled for 15 min. The reaction solution is stirred for 5 h at rt after which the HCl salt is recovered by filtration. The HCl salt is used in the next step without further purification.

General Procedure F

General Procedure for Removal of Boc Protecting Groups from Amino Groups

HCl gas is bubbled for 2 h into a solution of Boc amino acid in dry MeOH (100 mL) at rt. The reaction solution is stirred for 18 h at rt after which the product is recovered upon solvent removal. The HCl salt is used in the next step without further purification.

General Procedure G

General Procedure for Conversion of a Cyanophenyl Group to a 4,5-Dihydroimidazol-2-ylphenyl group A 3-[3-(R,S)-2-arylsulfonyl-4-oxo-2,5-benzodiazepin-3-yl]-N-[2-(p-cyanophenyl)eth-1-yl]acetamide compound (1.57 mmol) which can be prepared in a manner as described herein is dissolved in a solution of Et$_3$N/pyridine (6 mL/60 mL) at rt. H$_2$S is bubbled through for 15 min at rt. The reaction mixture is then capped and stirred at rt overnight. The solvent mixture is removed under reduced pressure and the resulting residue is then dissolved in a mixture of acetone/iodomethane (60 mL:5 mL). The solution is heated to reflux for 1.5 h whereupon the solvent is removed under reduced pressure. The crude material is dissolved in dry MeOH (15 mL), with Et$_3$N (1.0 eq.; 220 μL) and ethylenediamine (1.1 eq.; 120 μL). The solution is refluxed for 2 days. The solvent is evaporated under reduced pressure. The crude material can be purified by reverse phase HPLC (acetonitrile/water-0.1% TFA), and the resulting product isolated.

The process set forth in General Procedure H below is illustrated in the following reaction scheme:

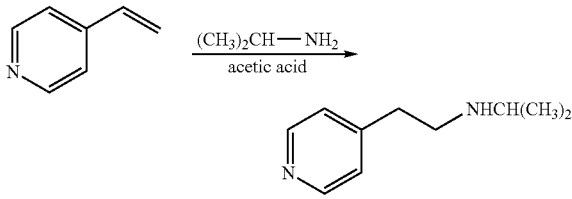

General Procedure H

General Procedure for Conversion of a Vinylpyridine Group to a 2-Aminoethylpyridine Group 4-Vinyl pyridine (1.6 mL; 15 mmol) is dissolved in acetic acid (12.5 mmol; 0.72 mL) and isopropylamine (12.5 mmol; 1.06 mL). The reaction mixture is refluxed for 6 h. The solvent is evaporated under reduced pressure. To the resulting solid is added EtOAc as well as saturated NaHCO$_3$. The organic layer is isolated, dried over MgSO$_4$. The solvent is removed under reduced pressure. The desired material is isolated as a foam.

H$^1$ NMR (CDCl$_3$) δ=8.4 (m, 2H); 7.05 (m, 2H); 2.75 (m, 2H); 2.65 (m, 3H); 0.99 (d, 6H). C$^{13}$ NMR (CDCl$_3$) 149.87; 149.54; 149.09; 123.93; 48.19; 47.20; 35.56; 22.43.

MS (API-ES)=165 (M+H).

The processes set forth in General Procedure I below are illustrated in the following reaction scheme:

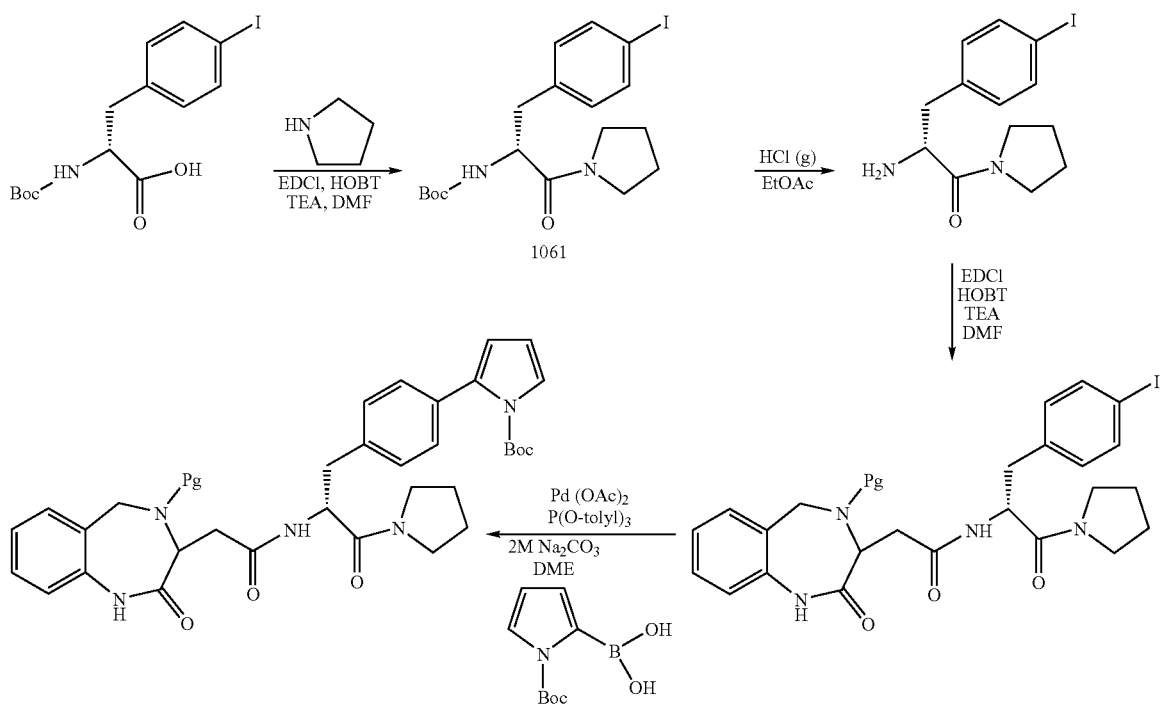

General Procedure I

General Procedure for Forming a Heteroaryl Substitution a Phenyl Group (D)-N-t-butoxycarbonyl-p-iodophenylalanine can be prepared by Boc protecting the commercially available p-iodophenylalanine (Aldrich). This compound can then be amidated by reaction with pyrrolidine using conventional coupling procedures to provide for 1-(R)-[1-(t-butoxycarbonyl-amino)-1-(pyrrolidin-1-ylcarbonyl)-2-(4-iodophenyl)] ethane and this amino acid derivative is sometimes referred to herein as compound 1061.

Removal of the Boc protecting group and coupling with a 3-[3-(R,S)-2-Pg-4-oxo-2,5-benzodiazepin-3-yl]acetic acid compound (Pg is a conventional protecting group which is orthogonally removed relative to the Boc protecting group), in a manner similar to that described herein affords the 3-[3-(R,S)-2-Pg-4-oxo-2,5-benzodiazepin-3-yl]-N-(R)-(1-pyrrolidin-1-ylcarbonyl-2-(4-iodophenyl)eth-1-yl)acetamide compound.

This compound (0.34 mmol) is dissolved in dry DME (6 mL) under nitrogen. To this is added Pd(OAc)$_2$ (0.1 eq.), P(O-tolyl)$_3$ (0.1 eq.), 2M Na$_2$CO$_3$ (1.7 mL) and 1-(t-butoxycarbonyl)pyrrole-2-boronic acid (2 eq.) (Frontier Scientific). The reaction mixture is stirred overnight at 80° C. The solvent is removed under vacuum and EtOAc (20 mL) is added. The organic layer is washed with H$_2$O (10 mL, 2×), brine (10 mL, 1×) and dried over Na$_2$SO$_4$. Upon filtration, the solvent is removed under vacuum and the desired product can be purified on column chromatography (silica gel).

The Pg protecting group can be removed using conventional methods and then the free amine is converted to contain the Q substituent as defined above. Since Pg is orthogonally removed relative to the Boc protecting group, its removal will result in retention of the Boc group. An example of a Pg group which is differentially removed (i.e., orthogonal) to the Boc protecting group is a CBZ protecting group.

Optionally and subsequently, the Boc protecting group on the pyrrolyl group can be removed in the manner described above.

The processes set forth in General Procedure J below are illustrated in the following reaction scheme:

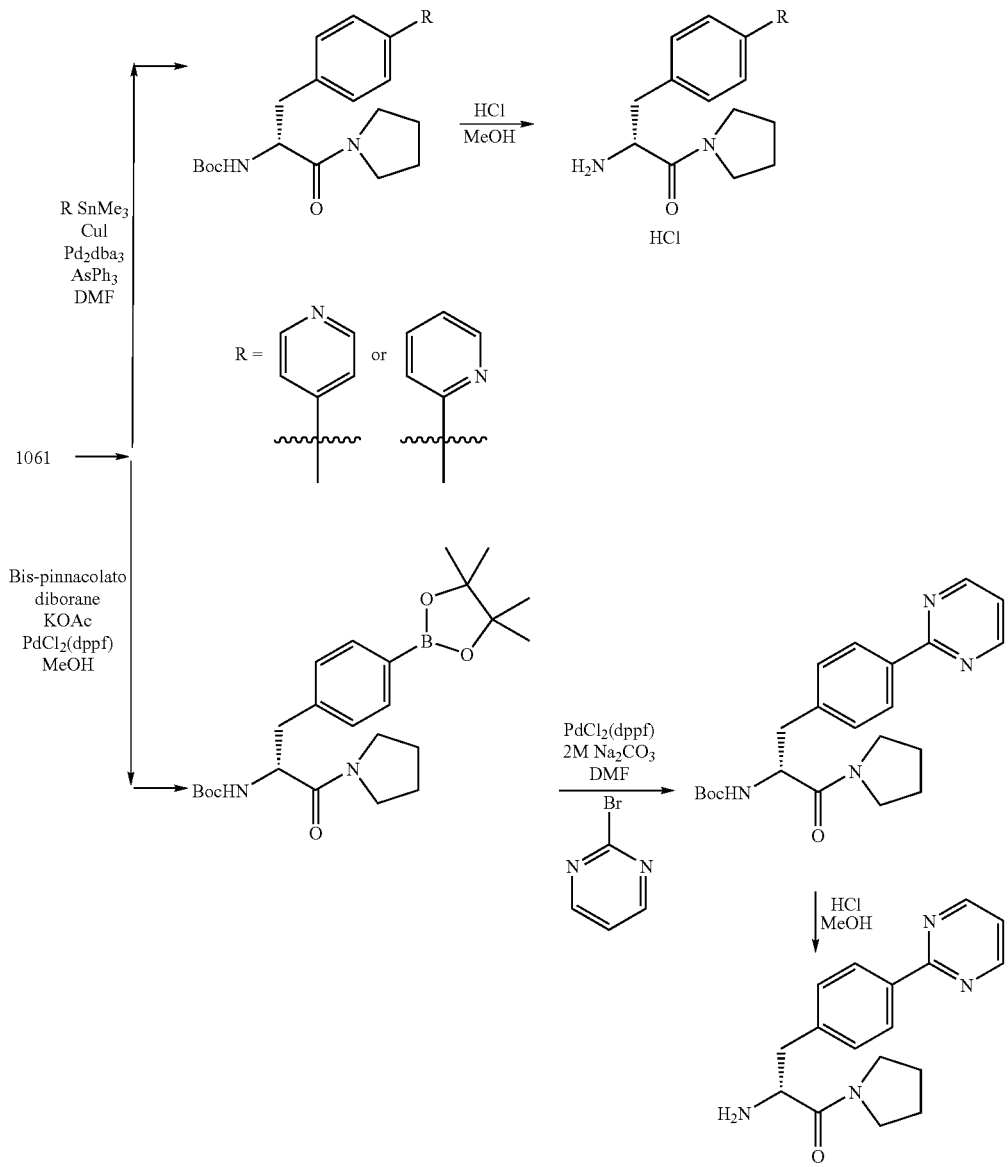

General Procedure J

General Procedure for Forming a 2- or 4-Pyridyl Substituent on a Phenyl Group Exemplified by the Preparation of 1-[(R)-1-Pyrrolidin-1-ylcarbonyl-1-amino-2-(4-(2-or 4-pyridyl)phenyl]ethane 1-(R)-[1-(t-butoxycarbonylamino)-1-(pyrrolidin-1-ylcarbonyl)-2-(4-iodophenyl)]ethane (compound 1061) (300 mg, 0.68 mmol), is added to a 50 mL round-bottom flask with CuI (8% mol) in dry DMF (10 mL). The resulting solution is flushed under nitrogen for 2–3 min. Pd$_2$dba$_3$ (2% mol) (Aldrich) and AsPh$_3$ (16% mol) (Aldrich) are weighed together in a small vial to which 1 mL of DMF is added. This solution is added to the reaction mixture and it is flushed under nitrogen for an additional 2–3 minutes. An oil bath is heated to 60° C. and the reaction mixture is immersed into it and allowed to thermally equilibrate. The commercially available pyridyl stannane (1.15 eq.) (Frontier) is then weighed out into a small vial to which 1 mL of DMF is added and this solution is then added to the previous reaction mixture and heated at 60° C. for 6 hours. The solvent is removed under vacuum. The crude residue is dissolved in EtOAc (30 mL). The organic layer is washed with brine (10 mL, 2×), and dried over MgSO$_4$. Upon filtration and evaporation of the solvent under reduced pressure, the crude material is purified on column chromatography (silica gel), eluted with EtOAc-Hexanes 3:2 to afford 1-[(R)-1-(pyrrolidin-1-ylcarbonyl)-1-(t-butoxycarbonylamino)-2-(4-(2-or 4-pyridyl)phenyl]ethane in good yield.

Subsequent removal of the Boc protecting group with HCl/methanol in the manner described above provides for the title compound as the HCl salt.

General Procedure K

General Procedure for Forming a 2-Pyrimidinyl Substituent on a Phenyl Group Exemplified by the Preparation of 1-[(R)-1-Pyrrolidin-1-ylcarbonyl-1-amino-2-(4-(2-pyrimidinyl)phenyl]ethane 1-(R)-[1-(t-butoxycarbonylamino)-1-(pyrrolidin-1-ylcarbonyl)-2-(4-iodophenyl)]ethane (compound 1061) (100 mg, 0.22 mmol), is dissolved in dry MeOH (5 mL) to which is added KOAc (1.5 eq.) and bis-pinnacolato diboron (1.1 eq.) (Aldrich) and the mixture is flushed under nitrogen for 5 minutes. The catalyst, PdCl$_2$(dppf) (0.03 eq.) (Aldrich), is then added and the reaction is heated at 60° C. overnight. The reaction mixture is filtered through Celite and condensed under vacuum. The residue is then treated with bromopyrimidine (3 eq.) (Aldrich), Na$_2$CO$_3$ (5 eq., 0.55 mL) and PdCl$_2$(dppf) (0.03 eq.) in DMF (1 mL) and is stirred at 80° C. overnight. The solvent is removed under vacuum. The crude residue is purified on column chromatography (silica gel), eluted with EtOAc-Hexanes, 3:2 to afford 1-[(R)-1-pyrrolidin-1-ylcarbonyl-1-(t-butoxycarbonylamino)-2-(4-(2-pyrimidinyl)phenyl]ethane in good yield.

Subsequent removal of the Boc protecting group with HCl/methanol in the manner described above provides for the title compound as the HCl salt.

The processes set forth in General Procedure L below are illustrated in the following reaction scheme:

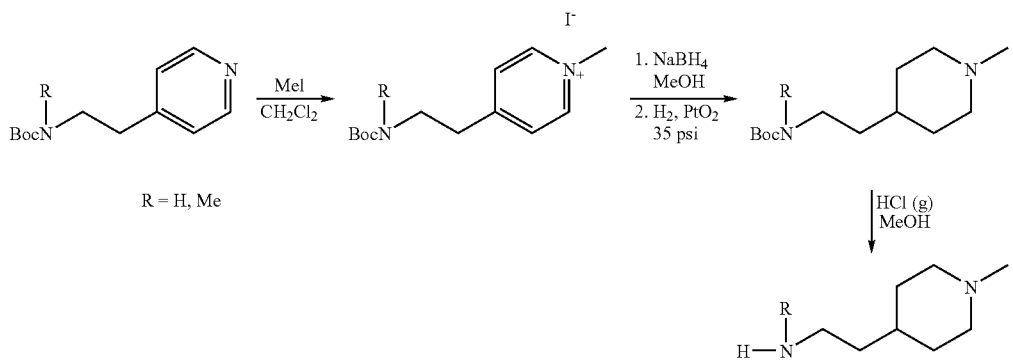

General Procedure L

General Procedure for the Preparation of 1.2,3,6-Tetrahydro-N-(Alkyl)pyridine derivatives Boc protected 2-aminoethylpyridine (or the N-methyl analog thereof) (120 mg, 0.18 mmol), is dissolved in MeOH/CH$_2$Cl$_2$ (2:1) to make a 2.5 M solution. To this is added MeI (4 eq.) and the mixture is heated in a sealed tube for 3.5 h. The solvent is removed under vacuum and the resulting crude mixture can be used directly without purification and/or isolation.

General Procedure M

General Procedure for the Reduction/Hydrogenation of a Pyridium Salt

The methyl pyridinium iodide salt produced above, (60 mg, 0.083 mmol), is dissolved in dry MeOH (4 mL) and the resulting mixture cooled to 0° C. Excess NaBH$_4$ was added and the mixture is allowed to stir for 30 min. The solvent is then removed under vacuum and water (5–10 mL) is added to the crude product and sonicated for 10 min. Upon filtration, the solvent is evaporated to provide for Boc protected 2-aminoethyl-1,2,5,6-tetrahydro-pyridine in good yields.

If desired, the remaining unsaturated bond in the Boc protected 2-aminoethyl-1,2,5,6-tetrahydropyridine can be hydrogenated with hydrogen/PtO$_2$maintained at about 35 psi.

The Boc protecting group of the saturated or unsaturated compound can then be removed by conventional methods (e.g., HCl/methanol).

The processes set forth in General Procedure N below are illustrated in the following reaction scheme:

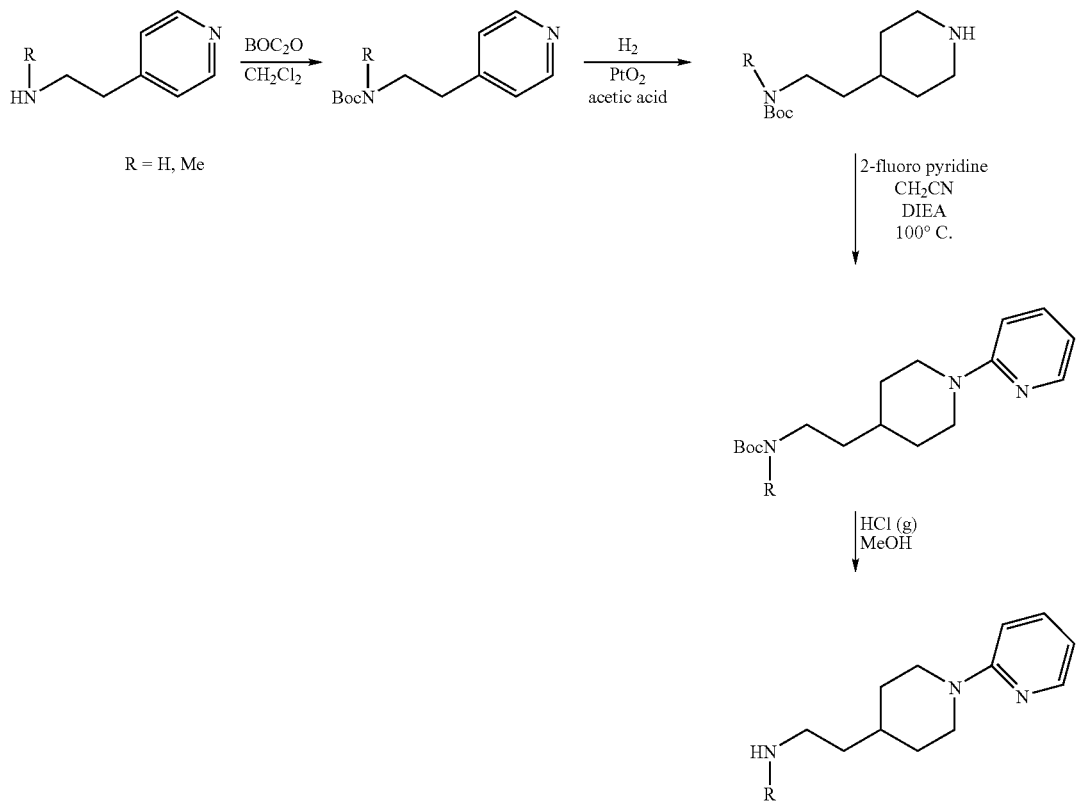

R = H, Me

General Procedure N

General Procedure for Preparing N-(pyrid-2-yl) piperidine Compounds Exemplified by the Preparation of 2-[1-(pyrid-2-yl)piperidin-4-yl]ethylamine

Step A: Synthesis of N-t-butoxycarbonyl 2-(pyrid-2-yl)ethylamine

4-Aminoethylpyridine (5.0 g, 40 mmol) and di-t-butyl dicarbonate (8.9 g, 40 mmol) are dissolved in $CH_2Cl_2$ (50 mL) and the resulting solution is stirred at rt for overnight. Solvent is removed under reduced pressure to afford N-t-butoxycarbonyl 2-(pyrid-2-yl)ethylamine as a reddish liquid (9.1 g, 100%).

Step B: Synthesis of N-t-butoxycarbonyl 2-(piperidin-2-yl)ethylamine

The product from step A is mixed with $PtO_2$ (640 mg) in HOAc (30 mL) and hydrogenation is carried out at 58 psi on a Parr apparatus overnight. Catalyst is removed and solvent is evaporated under reduced pressure to give N-t-butoxycarbonyl 2-(piperidin-2-yl)ethylamine as a black liquid.

Step C: Synthesis of N-t-butoxycarbonyl 2-[1-(pyrid-2-yl)piperidin-4-yl]ethylamine To a solution of N-t-butoxycarbonyl 2-(piperidin-2-yl) ethylamine (8.1 g) and DIEA (14.1 mL) in $CH_3CN$ (29 mL) is added 2-fluoropyridine (3.5 mL) and the resulting mixture is heated in a sealed-tube at 100° C. for three days. Solvent is removed and the crude product is purified via column chromatography (20% EtOAc/hexane) to afford 3.9 g of N-t-butoxycarbonyl 2-[1-(pyrid-2-yl)piperidin-4-yl]ethylamine.

$^1H$ NMR ($CDCl_3$) δ=8.16 (dd, J=1.8, 5.0 Hz, 1H), 7.44–7.38 (m, 1H), 6.61 (d, J=8.7 Hz, 1H), 6.53 (dd, J=5.0, 7.2, 1H), 4.58 (bs, 1H), 4.23 (d, J=12.6 Hz, 2H), 3.15 (q, J=6.6 Hz, 2H), 2.76 (dt, J=2.7, 12.6 Hz, 2H), 1.75 (d, J=12.6 Hz, 2H), 1.55–1.35 (m, 11H), 1.28–1.15 (m, 3H);

MS: m/z (EI+) 306 (M++H);

HPLC ($CH_3CN$—$H_2O$-0.1% TFA) (short column) Rt=2.27 min

Step D: Synthesis of 2-[1-(pyrid-2-yl)piperidin-4-yl]ethylamine

To a solution of N-t-butoxycarbonyl 2-[1-(pyrid-2-yl) piperidin-4-yl]ethylamine (3.9 g) in EtOAc (15 mL) was bubbled HCl (g) for 15 min. The suspension was then stirred under positive pressure ($N_2$) for 30 min. Solvent was removed under vacuum to afford the 2-[1-(pyrid-2-yl)piperidin-4-yl]ethylamine (pure) as the hydrochloride salt (white solid) (3.4 g, 98%).

The processes set forth in General Procedure O below are illustrated in the following reaction scheme:

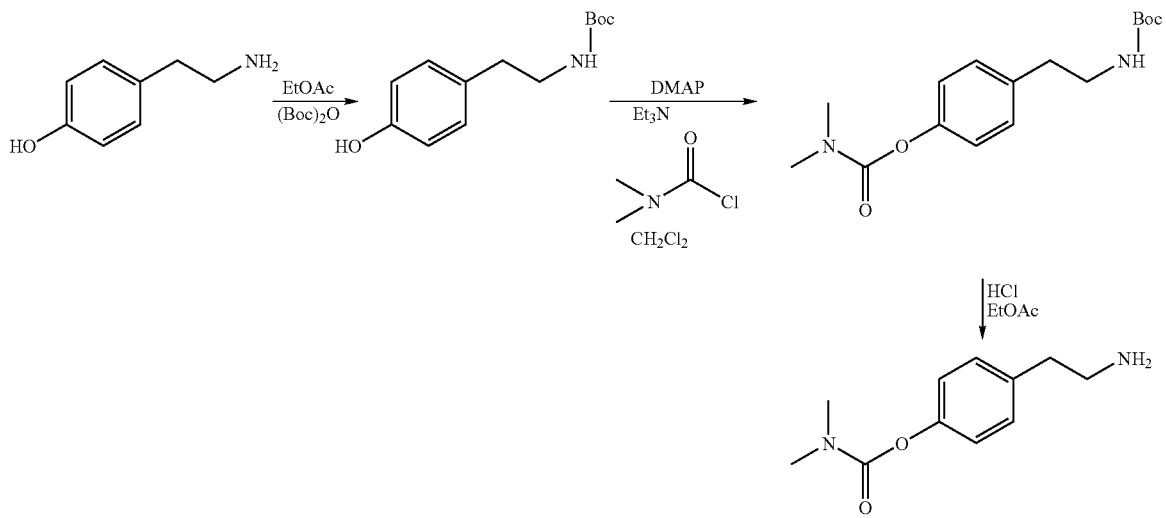

General Procedure O

General Procedure for the Preparation of Carbamoyloxy Substituted Phenylethyl Amine Compounds Exemplified by the Preparation of 2-[4-(N,N-dimethylaminocarbonyloxy)phenyl]ethylamine

Step A: Synthesis of N-t-butoxycarbonyloxy 2-(4-hydroxyphenyl)ethylamine

The amine group of 2-(4-hydroxyphenyl)ethylamine can be protected with a Boc protecting group in the manner described above to provide for N-t-butoxycarbonyloxy 2-(4-hydroxyphenyl)ethylamine.

Step B: Synthesis of N-t-butoxycarbonyloxy 2-[4-(N,N-dimethylaminocarbonyloxy)phenyl]ethylamine N-t-butoxycarbonyloxy 2-(4-hydroxyphenyl)ethylamine (2.53 g, 10.7 mmol), Et$_3$N (2.96 mL, 2 eq.), a catalytic amount of DMAP (131 mg) and dimethylcarbamyl chloride (2.0 mL, 2 eq.) are mixed in CH$_2$Cl$_2$ at 0° C. The resulting mixture is stirred overnight. EtOAc is added to dilute the reaction mixture and then is washed with 1N HCl, sat. Na$_2$CO$_3$ and brine. Solvent is removed under reduced pressure to give pure t-butoxycarbonyloxy 2-[4-(N,N-dimethylaminocarbonyloxy)phenyl]ethylamine as a colorless solid.

Step C: Synthesis of 2-[4-(N,N-dimethylaminocarbonyloxy)phenyl]ethylamine

The Boc protecting group on the t-Butoxycarbonyloxy 2-[4-(N,N-dimethylaminocarbonyloxy)phenyl]ethylamine is removed in a manner described above to provide for the title compound as a white solid, and this compound is used "as is" in the next step.

The processes set forth in General Procedure P below are illustrated in the following reaction scheme:

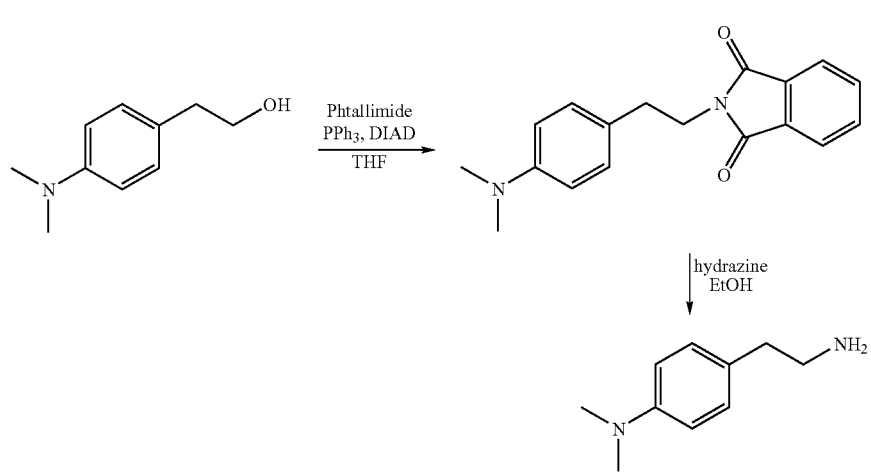

General Procedure P

General Procedure for Converting 2-[4-(N,N-dimethylaminophenyl]ethanol to 2-[4-(N,N-dimethylaminophenyl]ethylamine Step A: Synthesis of 2-[2-(4-N,N-dimethylaminophenyl)-ethyl]-isoindole-1,3-dione 2-[4-(N,N-dimethylaminophenyl]ethanol (2.05 g, 17.4 mmol), phthalimide (2.19 g, 14.9 mmol) and PPh$_3$ (3.93 g, 14.9 mmol) (Aldrich) are mixed in 100 mL of THF maintained at 0° C. The mixture is then treated with DIAD (2.68 mL) (Aldrich) which was added dropwise. After stirring overnight, the solvent is removed under reduced pressure to give a pale yellow solid. The solid is triturated with EtOAc three times. The combined EtOAc layers are treated with gaseous HCl to precipitate the product, and the desired product is isolated through filtration.

Step B: Synthesis of 2-[4-(N,N-dimethylaminophenyl]ethylamine

2-[2-(4-N,N-dimethylaminophenyl)-ethyl]-isoindole-1,3-dione (606 mg, 1.84 mmol) and hydrazine hydrate (30%, 0.64 mL) in ethanol is heated at 65° C. for 5 h. The precipitate is removed via filtration. The filtrate is concentrated to give the title compound as a white solid. This product is used in the next step without further purification.

The processes set forth in General Procedure Q below are illustrated in the following reaction scheme:

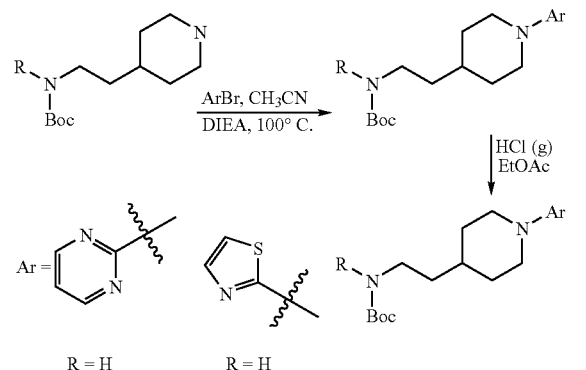

General Procedure Q

General Procedure for Preparing 2-[(1-Pyrimidin-2-yl)piperidin-4-yl]-ethylamine

Step A: Synthesis of N-t-butoxycarbonyloxy 2-[1-(pyrimidin-2-yl)piperidin-4-yl]-ethylamine N-t-butoxycarbonyloxy-2-(piperidin-4-yl)-ethylamine (as described above), DIEA (0.75 mL) and 2-bromopyrimidine (204 mg) (Aldrich) in acetonitrile (5 mL) are heated under reflux overnight. The solvent is removed under reduced pressure and the black liquid is subjected to a column chromatography, eluted with 1:1 EtOAc/hexanes, to give pure N-t-butoxy-carbonyloxy-2-[1-(pyrimidin-2-yl)piperidin-4-yl]-ethylamine as a pale yellow oil.

$^1$H NMR (CDCl$_3$) δ=8.21 (d, J=5.1 Hz, 2H), 6.36 (t, J=5.1 Hz, 1H), 4.64 (d, J=13.8 Hz, 2H), 3.14–3.07 (m, 2H), 2.76 (dt, J=2.7, 13.2 Hz, 1H), 1.69 (d, J=13.8 Hz, 1H), 1.57–1.30 (m, 11H), 1.20–1.03 (m, 3H);

MS: m/z (EI+) 307 (M++H); HPLC (CH$_3$CN—H2O-0.1% TFA) (short column) Rt=2.63 min.

Step B: Synthesis of 2-[(1-pydrimidin-2-yl)piperidin-4-yl]-ethylamine

The Boc protecting group on N-t-butoxy-carbonyloxy 2-[1-(pyrimidin-2-yl)piperidin-4-yl]-ethylamine is removed as described above to afford the title compound.

The processes set forth in General Procedure R below are illustrated in the following reaction scheme:

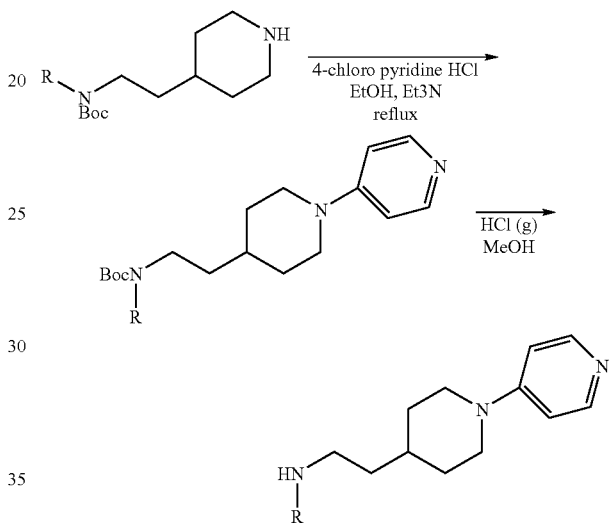

General Procedure R

General Procedure for Preparing N-(Pyrid-4-yl)piperidine Compounds

Step A: Synthesis of N-t-butoxycarbonyloxy 2-[1-(pyrid-4-yl)piperidin-4-yl]-ethylamine N-t-butoxycarbonyloxy 2-(piperidin-4-yl)-ethylamine (prepared as above) (14.4 g, 50 mmol), 4-chloropyridine HCl (1.0 eq., 8.0 g), TEA (2.2 eq.) are mixed in ethanol, and maintained under reflux overnight. The desired compound, N-t-butoxycarbonyloxy 2-[1-(pyrid-4-yl)piperidin-4-yl]-ethylamine, is isolated by column chromatography, (silica gel) eluted with EtOAc and carried to the next step.

Step B: Synthesis of 2-[1-(pyrid-4-yl)piperidin-4-yl]-ethylamine

The Boc protecting group on N-t-butoxycarbonyloxy 2-[1-(pyrid-4-yl)piperidin-4-yl]-ethylamine is then removed using procedures described above to provide the title compound.

The process set forth in General Procedure S below is illustrated in the following reaction scheme:

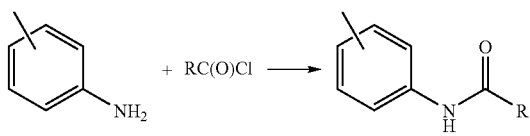

General Procedure S

To a solution of the starting aniline (100 mg; 0.19 mmol) in dry pyridine (5 mL), is added acetic anhydride (20 L). The mixture is stirred at rt overnight. Water (3 mL) is added to the mixture and the product was precipitated from the solution.

The following Examples illustrate the synthesis of certain intermediates and compounds of Formula I of this invention.

Example 1

Preparation of 3-[3-(R,S)-(4-chloro-2,5-dimethyl-benzenesulfonyl)-4-oxo-2,5-benzodiazepin-3-yl]-N-[2-(pyridin-4-yl)ethyl]acetamide (1)

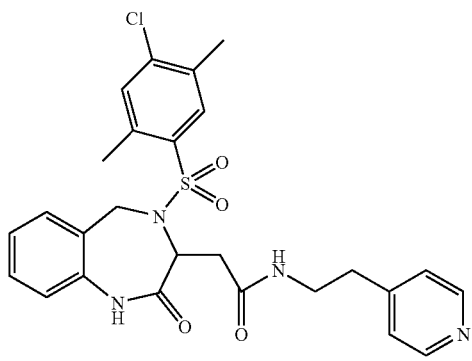

Step a): Preparation of 2-(2-nitrobenzylamino)succinic acid dimethyl ester

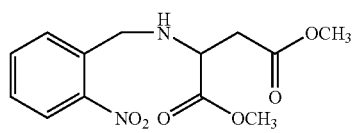

A mixture of D-aspartic acid dimethyl ester hydrochloride (4.2 g, 21.25 mmol) and sodium acetate (1.46 g, 17.85 mmol) was stirred in 25 mL of warm ethanol for 10 min. 2-Nitrobenzaldehyde (1.35 g, 8.936 mmol) was added and stirring was continued at room temperature for 1.5 h. Sodium cyanoborohydride (333.88 mg, 5.31 mmol) was added in portions over 5 min. and stirring at room temperature continued overnight. The reaction mixture was concentrated in vacuo, the residue was diluted with ethyl acetate and washed with saturated aqueous sodium bicarbonate and sodium chloride solutions. The organic layer was dried (Na$_2$SO$_4$) and concentrated to give 2.62 g of the title compound as a light brown oil.

MS(ES) m/e 297.1 [M+H]+

Step b): Preparation of 2-(2-aminobenzylamino)succinic acid dimethyl ester

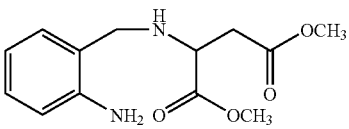

A mixture of 2-(2-nitrobenzylamino)succinic acid dimethyl ester [from a) above] (7.6 g, 25.65 mmol) and platinum oxide (349.51 mg, 1.54 mmol) was shaken in methanol on a Parr hydrogenation apparatus under 50 psi of hydrogen gas. After 12 h the mixture was filtered and concentrated to give 6.6 g of the title compound as a light brown oil.

MS(ES) m/e 267.1 [M+H]+

Step c): Preparation of [3-(R,S)-4-oxo-2,5-benzodiazepin-3-yl]acetic acid methyl ester

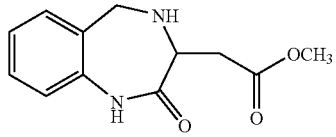

A 2.0 M solution trimethyl aluminum in toluene (20.5 mL, 1.10 mmol) was added dropwise to a solution of 2-(2-aminobenzylamino)succinic acid dimethyl ester from b) above (3.12 g, 11.72 mmol) in 50 mL of toluene maintained at 0° C. The solution was allowed to warm to room temperature and stirred for 1.5 h. The reaction was cooled to 0° C. and quenched with the dropwise addition of methanol. The resulting mixture was allowed to stir at room temperature for 1 h then diluted with an equal volume of ethyl acetate and treated with saturated aqueous sodium bicarbonate. The resulting slurry was filtered and the organic layer was separated. The aqueous layer was extracted with 3:1 chloroform/isopropanol solution and the organic layers were combined, dried (Na$_2$SO$_4$), and concentrated to give 2.13 g of the title compound as a yellow solid.

MS(ES) m/e 235.1 [M+H]+

Step d): Preparation of [3-(R,S)-2-(t-butoxycarbonyl)-4-oxo-2,5-benzodiazepin-3-yl]acetic acid methyl ester

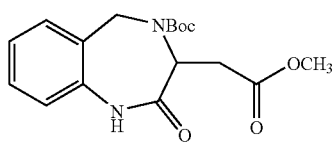

A solution of Preparation of [3-(R,S)-4-oxo-2,5-benzodiazepin-3-yl]acetic acid methyl ester from c) above (2.13 g, 9.09 mmol), di-tert-butyl dicarbonate (2.48 g, 11.37 mmol), and triethylamine (1.84 g, 2.53 mL, 18.18 mmol) in 50 mL of dichloromethane was stirred overnight at room temperature. Saturated aqueous sodium bicarbonate and catalytic DMAP was added and the mixture stirred for 1 h. The layers were separated and the organic phase was washed with saturated aqueous sodium chloride solution, dried (Na$_2$SO$_4$) and concentrated in vacuo. The solid residue was triturated with a solution of hexane in ethyl acetate to give the title compound (1.93 g) as a white powder.

MS(ES) m/e 335.1 [M+H]+

Step e): Preparation of [3-(R,S)-2-(t-butoxycarbonyl)-4-oxo-2,5-benzodiazepin-3-yl]acetic acid

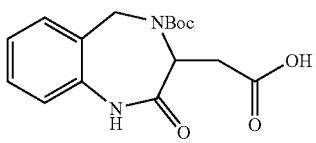

[3-(R,S)-2-(t-butoxycarbonyl)-4-oxo-2,5-benzodiazepin-3-yl]acetic acid methyl ester from d) above (1.0 g, 2.99 mmol) was dissolved in 60 mL of 3:2:1 THF/methanol/water and cooled to 0° C. A solution of lithium hydroxide (219 mg, 5.23 mmol) dissolved in a minimum of water was added and the resulting solution was stirred at 0° C. for 2.5 h. The reaction mixture was concentrated in vacuo and diluted with ethyl acetate and acidified with 10% aqueous sodium bisulfate solution. The layers were separated and the organic layer washed with saturated sodium chloride solution then dried (Na$_2$SO$_4$) and concentrated in vacuo to give the title compound (1 g) as a white solid.

MS(ES) m/e 343.0 [M+Na]+

Step f): Preparation of 3-[3-(R,S)-(4-chloro-2,5-dimethyl-benzenesulfonyl)-4-oxo-2,5-benzodiazepin-3-yl]-N-[2-pyridin-4-yl)ethyl]acetamide

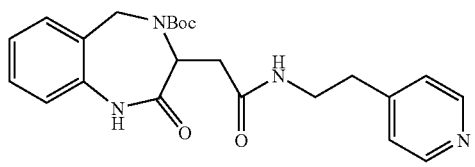

[3-(R,S)-2-(t-butoxycarbonyl)-4-oxo-2,5-benzodiazepin-3-yl]acetic acid from e) above (2 g, 6.24 mmol), was added to a solution of 2-pyridin-4-yl-ethylamine (953 mg, 7.8 mmol) and triethyl amine (1.9 mg, 2.61 L, 18.73 mmol) in 7 mL of DMF. The resulting solution was treated with diphenylphosporyl azide (2.23 mg, 1.75 mL, 8.12 mmol) and stirred at room temperature overnight. The reaction was concentrated in vacuo and treated with a small amount of saturated aqueous sodium bicarbonate solution. After 1 h a solid precipitated and was filtered, washed with water and air dried to give the title compound (2.69 mg).

MS(ES) m/e 425.2 [M+Na]+

Step g: Preparation of 3-[3-(R,S)-(4-chloro-2,5-dimethylbenzene-sulfonyl)-4-oxo-2.5-benzodiazepin-3-yl]-N-[2-(pyridin-4-yl)ethyl]acetamide

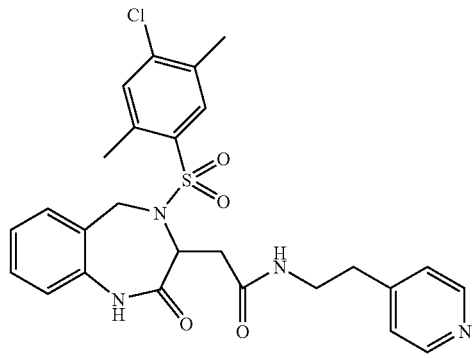

3-[3-(R,S)-(4-chloro-2,5-dimethyl-benzenesulfonyl)-4-oxo-2,5-benzodiazepin-3-yl]-N-[2-(pyridin-4-yl)ethyl]acetamide from f) above was dissolved in formic acid and heated to 40° C. for 2 h. The reaction was concentrated and the residue was dissolved in a 3:1 mixture of chloroform and isopropanol. The organic phase was neutralized with saturated aqueous sodium bicarbonate, then dried (Na$_2$SO$_4$) and concentrated to give a viscous oil (340 mg). The oil was dissolved in pyridine, cooled to 0° C. and treated with 4-chloro-2,5-dimethyl-benzenesulfonyl chloride (687 mg, 2.88 mmol). The solution was allowed to warm to room temperature and stirred overnight. The reaction was quenched with the addition of catalytic DMAP and saturated aqueous sodium bicarbonate then concentrated in vacuo. The residue was taken up in a mixture of 3:1 chloroform and isopropanol and washed with saturated aqueous sodium bicarbonate and saturated aqueous sodium chloride solutions then dried (Na$_2$SO$_4$) and concentrated to give a brown residue. Column chromatography (methanol in dichloromethane) afforded the title compound as a pure tan solid (218 mg).

$^1$H NMR (CD$_3$OD) δ=8.44 (d, J=4.5, 2H), 7.63 (s, 1H), 7.33 (d, J=5.4, 2H), 7.20–7.14 (m, 2H), 7.08(d, J=6.3, 1H), 7.00–6.94 (m, 1H), 6.87 (d, J=7.8, 1H), 5.10 (t, J=6.6, 1H), 4.67 (d, J=16.2, 1H), 4.52 (d, J=16.2, 1H), 3.40 (t, J=6.9, 2H), 2.84 (t, J=7.2, 2H), 2.73–2.70 (m, 2H), 2.42 (s, 3H), 2.28 (s, 3H)

MS(ES) m/e 527.1 [M+H]+

Example 2

Preparation of
2-chloro-(4-chloro-2,5-dimethylphenyl)acetophenone

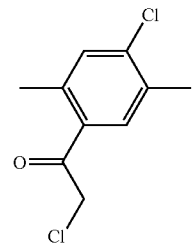

A mixture of 2-chloro-1,4-dimethyl-benzene (5 g, 35.56 mmol) and chloroacetylchloride (4.0 g, 35.6 mmol) was cooled to 0° C. and treated with aluminum chloride (4.74 g, 35.6 mmol) in small portions. The reaction slurry was diluted with dichloromethane and allowed to warm to room temperature. After 30 min the reaction was poured onto a mixture of ice and 10 mL of concentrated aqueous hydrochloric acid solution. The mixture was extracted with ethyl acetate and the organic layers were combined and washed with saturated aqueous sodium bicarbonate solution. The organic layer was separated, dried ($Na_2SO_4$) and concentrated to give approximately 7 g of pure product as a white powder.

MS(ES) m/e 217.1 [M+H]+

Example 3

Preparation of (2-amino-1-cyclopropyl-1-pridin-4-yl)ethyl

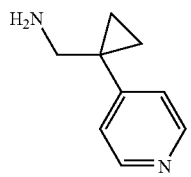

A mixture of pyridin-4-yl-acetonitrile (1.2 g, 7.76 mmol), benzyltriethylammonium bromide (63 mg, 0.23 mmol), and 1-bromo-2-chloro-ethane (16.7 g, 116.4 mmol) at 50° C. was treated with the dropwise addition of 50% aqueous sodium hydroxide over 15 minutes. Stirring continued at 50° C. for 2 h then at room temperature for an additional 2 h. The reaction mixture was diluted with water and extracted several times with dichloromethane. The organic layers were combined, washed with water then separated, dried ($Na_2SO_4$) and concentrated to give 1.2 g of pure product as a red brown solid. The solid was dissolved in 20 mL of 2N ammonium in methanol and treated with a catalytic amount of Raney-Nickel in water. The resulting mixture was shaken overnight under 50 psi of hydrogen. The mixture was filtered and concentrated to give 740 mg of a light tan oil.

MS(ES) m/e 149.2 [M+H]+

Example 4

Preparation of 3-[3-(R,S)-(4-chloro-2,5-dimethyl-benzenesulfonyl)-4-oxo-2,5-benzodiazepin-3-yl]-N-[2-(1,2,5,6-tetrahydro-N-methylpyridin-4-yl)eth-1-yl]acetamide (2)

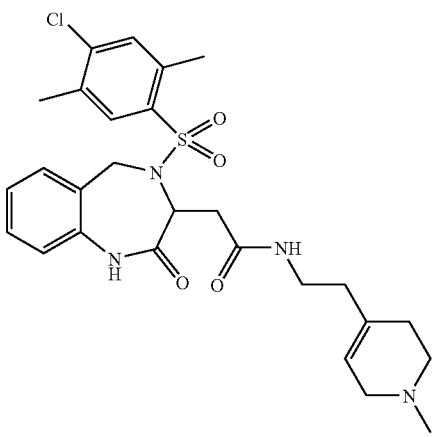

The compound made in Example 1 was dissolved in DMF (186 mg, 0.3 mmol) and treated with methyl iodide (430.9 mg, 189 μL, 3.04 mmol). The reaction was stirred at room temperature overnight, then concentrated in vacuo. The residue was taken up in methanol and treated with sodium borohydride (35 mg, 0.9 mmol) in portions and stirred for 1 h at room temperature. The mixture was concentrated and the residue was triturated with a solution of hexane and ethyl acetate to give 70 mg of pure product.

$^1$H NMR δ ($CD_3OD$) 7.65 (s, 1H), 7.22–7.11 (m, 3H), 6.99 (t, J=7.3, 1H), 6.90 (d, J=7.8, 1H), 5.44 (s, 1H), 5.06 (t, J=6.7, 1H), 4.74 (d, J=15.3, 1H), 4.58 (d, J=15.3, 1H), 3.20 (dt, Jd=2.4, Jt=7.0, 2H), 2.94 (s, 2H), 2.70 (d, J=7.2, 2H), 2.59 (t, J=5.5, 2H), 2.44 (s, 3H), 2.34 (s, 3H), 2.29 (s, 3H), 2.14 (t, J=6.3, 4H)

MS(ES) m/e 545.4 [M+H]+

Example 5

Preparation of 3-[3-(R,S)-(4-chloro-2,5-dimethyl-benzenesulfonyl)-2-oxo-2,5-benzodiazepin-3-yl]-N-[2-(N-methylpiperidin-4-yl)eth-1-yl]acetamide (3)

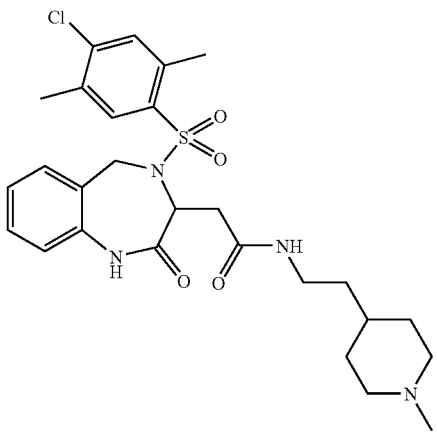

The compound made in Example 4 was dissolved in methanol and shaken in a Parr apparatus with platinum oxide (62 mg, 0.27 mmol) under 50 psi of hydrogen gas for 12 h. The mixture was filtered and concentrated and the residue was purified by preparative HPLC to give the title compound (19.2 mg) as a pure solid.

$^1$H NMR ($CD_3OD$) δ=7.55 (s, 1H), 7.18–7.11 (m, 3H), 7.00–6.95 (m, 1H), 6.80 (d, J=8.1, 1H), 5.24–5.19 (m, 1H), 4.74 (d, J=15.3, 1H), 4.60 (d, J=15.3, 1H), 3.50–3.46 (m, 1H), 3.21–3.13 (m, 1H), 3.02 (t, J=13.0, 2H), 2.87–2.70 (m, 2H), 2.83 (s, 3H), 2.43 (s, 3H), 2.23 (s, 3H), 2.15–2.01 (m, 2H), 1.77–1.69 (m, 1H), 1.5–1.34 (m, 3H)

MS(ES) m/e 547.4 [M+H]+

Example 6

Preparation of 3-[3-(R,S)-(4-chloro-2,5-dimethyl-benzenesulfonyl)-2-oxo-2,5-benzodiazepin-3-yl]-N-[2-(N-{pyrid-4-yl}piperidin-4-yl)eth-1-yl]acetamide (4)

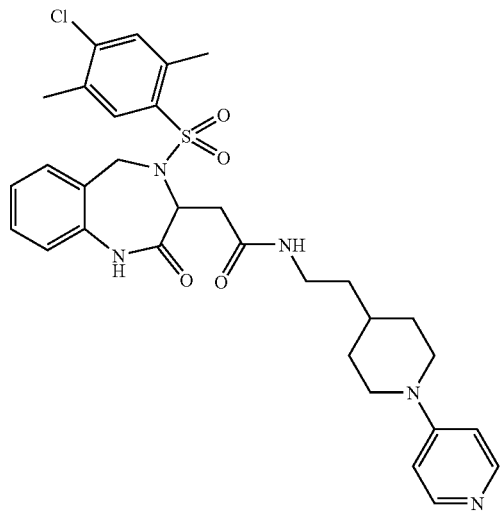

The title compound was prepared (3.1 mg) using the procedures outlined in Example 1, substituting 2-(N-(pyrid-4-yl)piperidin-4-yl)eth-1-ylamine in step (f), as an HCl salt.
MS(ES) m/e 611.2 [M+H]+

Example 7

Preparation of 3-[3-(R or S)-(4-chloro-2,5-dimethylbenzenesulfonyl)-4-oxo-2,5-benzodiazepin-3-yl]-N-[2-(pyridin-4-yl)ethyl]acetamide (9 or 10)

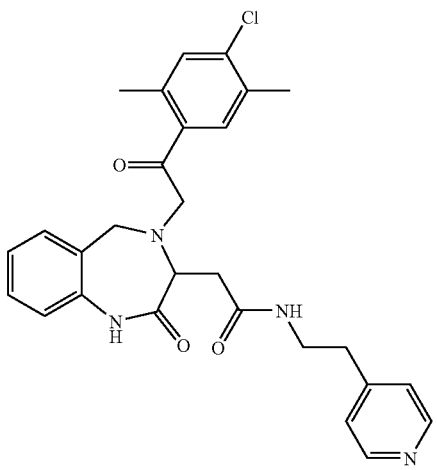

The compound made in Example 1(f) was dissolved in formic acid and heated to 40 C for 2 h. The reaction was concentrated and the residue was dissolved in a 3:1 mixture of chloroform and isopropanol. The organic phase was neutralized with saturated aqueous sodium bicarbonate, then dried (Na$_2$SO$_4$) and concentrated to give a viscous oil. The oil was dissolved in a minimum amount of DMF and treated with 2-chloro-(4-chloro-2,5-dimethylphenyl)acetophenone, prepared according to Example 2 (112.51 mg, 052 mmol), triethylamine (95.35 mg, 131 μL, 0.94 mmol), and catalytic potassium iodide, then heated to 80 C for 1.5 h. The reaction mixture was cooled and concentrated. The resulting residue was taken up in a solution of 3:1 chloroform/isopropanol and extracted with saturated aqueous sodium bicarbonate. The organic phase was dried (Na$_2$SO$_4$) and concentrated to give an orange solid. Flash chromatography gave the title compound as a yellow solid (20 mg).

$^1$H NMR ((CD$_3$)$_2$SO) δ=10.0 (s, 1H), 8.46–8.43 (m, 1H), 7.98 (t, J=5.7, 1H), 7.63 (s, 1H), 7.39 (s, 1H), 7.20–7.14 (m, 4H), 7.03–6.92 (m, 2H), 4.75 (t, J=6.9, 1H), 4.66 (d, J=16.8, 1H), 4.51 (d, J=16.8, 1H), 3.26–3.13 (m, 4H), 2.66–2.52 (m, 6H), 2.37 (s, 3H), 2.27 (s, 3H).
MS(ES) m/e 505.1 [M+H]+

Example 8

Preparation of 3-[3-(R,S)-(4-chloro-2,5-dimethyl-benzenesulfonyl)-2-oxo-2,5-benzodiazepin-3-yl]-N-[4-(pyridin-2-yl)piperazin-1-yl]acetamide (6)

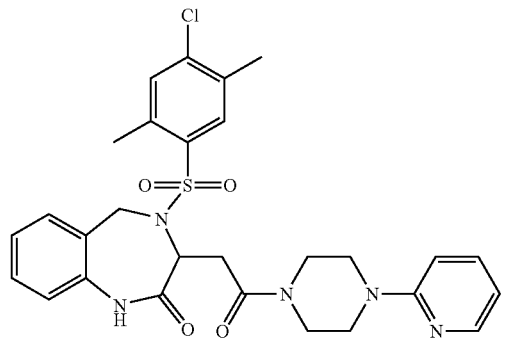

The title compound was prepared (400.0 mg) using the procedures described in Example 1, substituting 1-pyridin-2-ylpiperazine in step (f).

$^1$H NMR ((CD$_3$)$_2$SO) δ=10.14 (s, 1H), 8.13–8.10 (m, 1H), 7.66 (s, 1H), 7.58–7.52 (m, 1H), 7.39 (s, 1H), 7.21–7.17 (m, 2H), 7.04 (d, J=8.1, 1H), 6.96 (t, J=7.4, 1H), 6.81 (d, J=8.4, 1H), 6.68–6.64 (m, 1H), 4.87–4.81 (m, 2H), 4.55 (d, J=16.8, 1H), 2.86 (d, J=6.6, 1H), 2.40 (s, 3H), 2.25 (s, 3H)
MS(ES) m/e 569.2 [M+H]+

Example 9

Preparation of 3-[3-(R,S)-(4-chloro-2,5-dimethyl-benzenesulfonyl)-2-oxo-2,5-benzodiazepin-3-yl]-N-[4-(pyridin-4-yl)piperazin-1-yl]acetamide (7)

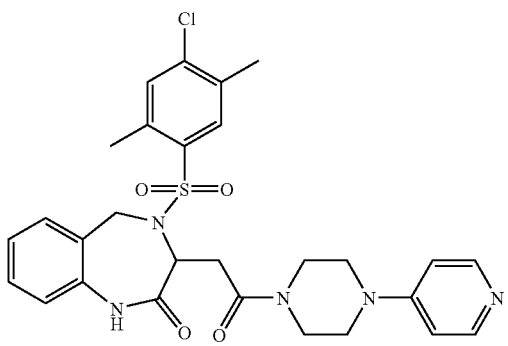

The title compound was prepared (350.0 mg) using the procedures described in Example 1, substituting 1-pyridin-4-ylpiperazine in step (f).

¹H NMR ((CD₃)₂SO) δ=10.1 (s, 1H), 8.26 (d, J=7.2, 1H), 7.64 (s, 1H), 7.37 (s, 1H), 7.21–7.14 (m, 3H), 7.03–6.93 (m, 2H), 4.88 (t, J=6.4, 1H), 4.82 (d, J=16.8, 1H), 4.63 (d, J=16.8, 1H), 3.68–3.59 (m, 4H), 3.22–3.04 (m, 4H), 2.92–2.89 (m, 1H), 2.38 (s, 3H), 2.25 (s, 3H).

MS(ES) m/e 569.2 [M+H]+

Example 10

Preparation of 3-[3-(R,S)-(4-chloro-2,5-dimethyl-benzenesulfonyl)-2-oxo-2,5-benzodiazepin-3-yl]-N-[2-cyclopropyl-2-(pyridin-4-yl)eth-1-yl]acetamide (8)

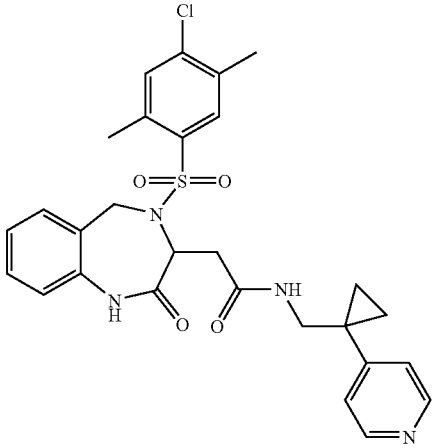

The title compound was prepared using the procedures described in Example 1, substituting C-(1-pyridin-4-ylcyclopropyl)methylamine in step (f), and was ultimately isolated as the TFA salt after preparatory HPLC (70.4 mg).

¹H NMR ((CD₃)₂SO) δ=10.0 (s, 1H), 8.64 (d, J=5.1, 1H), 8.14 (t, J=5.4, 1H), 7.61–7.58 (m, 3H), 7.38 (s, 1H), 7.18–7.13 (m, 2H), 6.98–6.91 (m, 2H), 4.81 (t, J=6.4, 1H), 4.67 (d, J=16.8, 1H), 4.49 (d, J=16.8, 1H), 2.62–2.55 (m, 4H), 2.35 (s, 3H), 2.25 (s, 3H), 1.22 (s, 2H), 1.14 (s, 2H).

MS(ES) m/e 553.5 [M+H]+

Example 11

Preparation 3-[3-(R,S)-(2,3-dichlorobenzenesulfonyl)-2-oxo-2,5-benzodiazepin-3-yl]-N-[2-(R,S)-cyclopropyl-2-(pyridin-4-yl)eth-1-yl]acetamide (11)

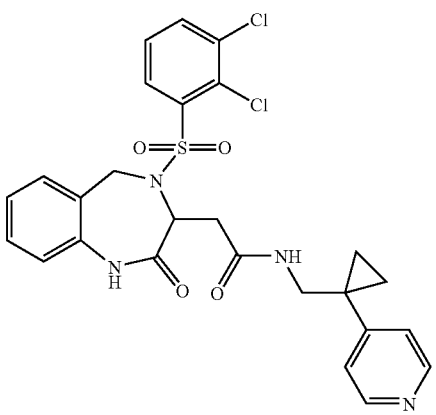

The title compound was prepared using the procedures of Example 10, substituting 2,3-dichlorobenzenesulfonyl chloride in step (g) of Example 1, and was ultimately isolated as the TFA salt after preparatory HPLC (109 mg).

¹H NMR ((CD₃)₂SO) δ=10.14 (s, 1H), 8.69 (d, J=6, 2H), 8.20 (t, J=5.2, 1H), 7.90–7.81 (m, 2H), 7.68 (d, J=6.0, 2H), 7.45 (t, J=7.8, 1H), 7.00 (t, J=7.5, 2H), 6.82 (t, J=7.2, 1H), 4.96–4.91 (m, 1H), 4.76 (d, J=16.8, 1H), 4.59 (d, J=16.8, 1H), 2.79–2.59 (m, 2H), 1.28–1.18 (m, 6H)

MS(ES) m/e 559.0 [M+H]+

Example 12

Preparation of 3-[3-(R,S)-(2,3-dichlorobenzenesulfonyl)-2-oxo-2,5-benzodiazepin-3-yl]-N-[2-(N-{pyridin-2-yl}piperidin-4-yl)eth-1-yl]acetamide (13)

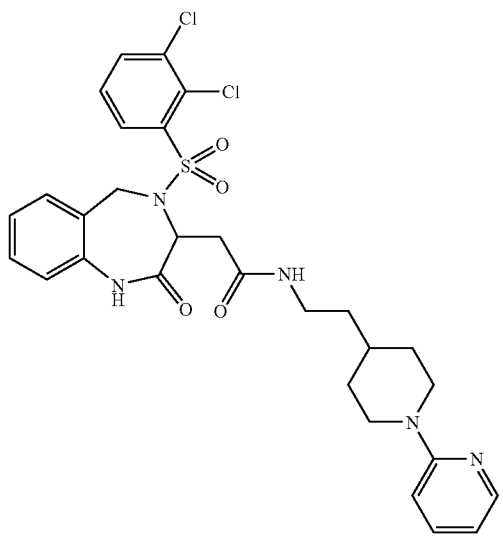

The title compound was prepared using the procedures described in Example 11, substituting 2-(N-(pyrid-2-yl)piperidin-4-yl)eth-1-ylamine in step (f) of Example 1, and was ultimately isolated as the TFA salt after preparatory HPLC (25 mg).

¹H NMR (CD₃OD) δ=8.14 (t, J=5.7, 1H), 8.00–7.84 (m, 4H), 7.60 (d, J=9.3, 1H), 7.38 (d, J=9.3, 1H), 7.30 (t, J=9.3, 1H), 7.10–7.04 (m, 1H), 6.92–6.71 (m, 4H), 5.46–5.41 (m, 1H), 4.80 (d, J=15.9, 1H), 4.60 (d, J=15.9, 1H), 4.14 (d, J=13.8, 1H), 3.01–2.85 (m, 2H), 2.04–1.96 (m, 1H), 1.92–1.82 (m, 1H), 1.56–1.49 (m, 2H), 1.40–1.25 (m, 2H).

MS(ES) m/e 616.1 [M+H]+

Example 13

Preparation of 3-[3-(R,S)-(4-chloro-2,5-dimethyl-benzenesulfonyl)-2-oxo-2,5-benzodiazepin-3-yl]-N-[2-(N-oxopyridin-4-yl)eth-1-yl]acetamide (5)

The title compound was prepared using procedures and methods of the invention as described above.

¹H NMR (CD₃OD) δ=8.24 (d, J=5.7, 2H), 7.61 (s, 1H), 7.45 (d, J=6.6, 1H), 7.18–7.13 (m, 2H), 7.07 (d, J=6.9, 1H), 6.95 (t, J=7.2, 1H), 6.86 (d, J=7.2, 1H), 5.11 (t, J=6.1, 1H), 4.68 (d, J=16.2, 1H), 4.53 (d, J=16.2, 1H), 3.44–3.40 (m, 2H), 2.87 (t, J=6.1, 2H), 2.71 (t, J=5.7, 2H), 2.40 (s, 3H), 2.26 (s, 3H).

Example 14

Preparation of 3-[3-(R,S)-(2,3-dichlorobenzene-sulfonyl)-4-oxo-2,5-benzodiazepin-3-yl]-N-[2-(pyridin-4-yl)ethyl]acetamide (12)

The title compound can be prepared using procedures and methods of the invention as described above.

Example 15

Preparation of 3-[3-(R,S)-(4-chloro-2,5-dimethylphenylcarbonylmethyl)-2-oxo-2,5-benzodiazepin-3-yl]-N-[2-pyridin-4-yleth-1-yl]acetamide (14)

The title compound was prepared using procedures and methods of the invention as described above.
$^1$H NMR (CD$_3$OD) δ=8.30 (d, J=4.2, 1H), 7.61 (s, 1H), 7.35–7.29 (m, 2H), 7.21–7.07 (m, 2H), 4.00–3.75 (m, 3H), 3.52–3.27 (m, 1H), 2.82 (t, J=7.0, 1H), 2.73 (dd, J=15.9, J=7.5, 1H), 2.47–2.40 (m, 1H), 2.42 (s, 3H), 2.34 (s, 3).

From the foregoing description, various modifications and changes in the composition and method will occur to those skilled in the art. All such modifications coming within the scope of the appended claims are intended to be included therein.

Biological Example

The potency and efficacy to inhibit the bradykinin B1 receptor was determined for the compounds of this invention in a cell-based fluorescent calcium-mobilization assay. The assay measures the ability of test compounds to inhibit B1 agonist-induced increase of intracellular free°Ca+2 in a native human B1 receptor-expressing cell line.

In this example, the following additional abbreviations have the meanings set forth below. Abbreviations heretofore defined are as defined previously. Undefined abbreviations have there art recognized meanings.

| | |
|---|---|
| BSA = | bovine serum albumin |
| DMSO = | Dimethylsulfoxide |
| FBS = | fetal bovine serum |
| MEM = | minimum essential medium |
| mM = | millimolar |
| ng = | nanogram |
| μg = | microgram |
| M = | molar |
| μM = | micromolar |

Specifically, calcium indicator-loaded cells are pre-incubated in the absence or presence of different concentrations of test compounds followed by stimulation with selective B1 agonist peptide while Ca-dependent fluorescence is monitored.

IMR-90 human lung fibroblast cells (CCL 186, American Type Tissue Collection—ATTC) are grown in MEM supplemented with 10% FBS as recommended by ATCC. Confluent cells are harvested by trypsinization and seeded into black wall/clear bottom 96-well plates (Costar #3904) at approximately 1,000 cells/well. The following day, cells are treated with 0.35 ng/mL interleukin-1β in 10% FBS/MEM for 2 hours to up-regulate B1 receptors. Induced cells are loaded with fluorescent calcium indicator by incubation with 2.3 μM Fluo-4/AM (Molecular Probes) at 37° C. for 1.5 hrs in the presence of an anion transport inhibitor (2.5 mM probenecid in 1% FBS/MEM). Extracellular dye is removed by washing with assay buffer (2.5 mM probenecid, 0.1% BSA, 20 mM HEPES in Hank's Balanced Salt Solution without bicarbonate or phenol red, pH 7.5) and cell plates are kept in dark until used. Test compounds are assayed at 7 concentrations in triplicate wells. Serial dilutions are made in half log-steps at 100-times final concentration in DMSO and then diluted in assay buffer. Compound addition plates contain 2.5-times final concentrations of test compounds or controls in 2.5% DMSO/assay buffer. Agonist plates contain 5-times the final concentration of 2.5 mM (3×EC$_{50}$) B1 agonist peptide des-Arg10-kallidin (DAKD, Bachem) in assay buffer. Addition of test compounds to cell plate, incubation for 5 min at 35° C., followed by the addition of B1 agonist DAKD is carried out in the Fluorometric Imaging Plate Reader (FLIPR, Molecular Devices) while continuously monitoring Ca-dependent fluorescence. Peak height of DAKD-induced fluorescence is plotted as function of concentration of test compounds. IC$_{50}$ values are calculated by fitting a 4-parameter logistic function to the concentration-response data using non-linear regression (Xlfit, IDBS).

Typical potencies observed for B1 receptor agonist peptides are EC50 approximately 0.8 nM and approximately 100 nM for des-Arg10-kallidin and des-Arg9-bradykinin, respectively, while for B1 antagonist peptide des-Arg10, Leu9-kallidin IC50 is approximately 1 nM.

The compounds prepared above exhibited IC$_{50}$ values of 0.1 to 10,000 nM in this assay.

In view of the above, all of these compounds exhibit B1 antagonistic properties and, accordingly, are useful in treating disease conditions mediated at least in part by B1.

From the foregoing description, various modifications and changes in the above described invention will occur to those skilled in the art. All such modifications coming within the scope of the appended claims are intended to be included therein.

What is claimed is:
1. A compound of the formula:

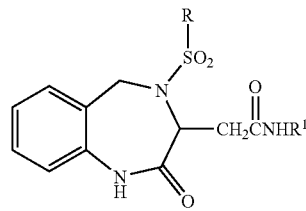

wherein
R is selected from the group consisting of aryl, substituted aryl, heteroaryl, substituted heteroaryl, heterocyclic and substituted heterocyclic; and
R$^1$ is selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic; or
pharmaceutically acceptable salts, tautomers or isomers thereof.

2. A compound according to claim 1 wherein R is selected from the group consisting of phenyl; naphth-1-yl; 5-dimethylaminonaphth-1-yl; 2-fluorophenyl; 2-chlorophenyl; 2-cyanophenyl; 2-methylphenyl; 2-nitrophenyl; 2-trifluoromethylphenyl; 3-chlorophenyl; 4-methylphenyl (tolyl); 2,5-dibromophenyl; 4-bromo-2-ethylphenyl; 4-bromo-2-trifluoromethoxy-phenyl; 2,3-dichlorophenyl; 2,4-dichlorophenyl; 3,4-dichlorophenyl; 2,5-dichlorophenyl; 2,6-dichlorophenyl; 2-chloro-4-cyanophenyl; 2-chloro-4-fluorophenyl; 3-chloro-2-methylphenyl; 2-chloro-6-methylphenyl; 5-chloro-2-methoxyphenyl; 2-chloro-4-trifluoromethylphenyl; 2,4-difluorophenyl; 5-fluoro-2-methylphenyl; 2,5-dimethoxyphenyl; 2-methoxy-4-methylphenyl; 2-methoxy-5-bromophenyl; 2-methoxy-5-methylphenyl; 2,5-dimethylphenyl; 2-methyl-5-nitrophenyl; 3,5-di(trifluoromethyl)phenyl; 4-bromo-2,5-difluorophenyl; 2,3,4-trichlorophenyl; 2,4,5-trichlorophenyl; 2,4,6-trichlorophenyl; 2,4-dichloro-5-methylphenyl; 4-chloro-2,5-dimethylphenyl; 2,4,6-tri(iso)propylphenyl; 2,4,6-trimethylphenyl; 2,3,5-trimethyl-4-chlorophenyl; 2,3,6-trimethyl-4-methoxyphenyl; 2,3,4,5,6-pentamethylphenyl; 5-chloro-1,3-dimethylpyrazol-4-yl; 2-methoxycarbonylthiophen-3-yl; 2,3-dimethylimidazol-5yl; 2-methylcarbonylamino-4-methyl-thiazol-5-yl; quinolin-8-yl; thiophen-2-yl; 1-methylimidiazol-4-yl; 3,5-dimethylisoxazol-4-yl; and N-morpholino.

3. The compound according to claim 2 wherein R is selected from the group consisting of 4-chloro-2,5-dimethylphenyl and 2,3-dichlorophenyl.

4. The compound according to claim 1 wherein $R^1$ is selected from the group consisting of:

2-[(4-amidino)phenyl]-1-(R)-(pyrrolidin-N-ylcarbonyl)eth-1-yl,
2-[N-(-aminoacetyl)piperid-4-yl]eth-1-yl,
4-aminobenzyl, 2-[4-(aminoethyleneamidino)phenyl]eth-1-yl,
2-[N-(1-amino-1-methylethylcarbonyl)piperid-4-yl]eth-1-yl,
2-(4-aminophenyl)eth-1-yl,
2-aminothiazol-5-ylmethyl,
(2-aminopyrid-4-yl)methyl,
benzyl,
2-bromoeth-1-yl,
1-(S)-carboxamide-2-(indol-3-yl)eth-1-yl,
carboxamidemethyl,
1-carboxamide-2-(S)-methyl-but-1-yl,
1-(S)-carbamyol-2-(phenyl)eth-1-yl,
1-(R)-carboxamide-2-(phenyl)eth-1-yl,
4-carboxybenzyl,
2-chloroeth-1-yl,
cyanomethyl,
2-(4-cyanophenyl)eth-1-yl,
2-(4-cyanophenyl)-1-(R)-(pyrrolidin-N-ylcarbonyl)eth-1-yl,
2-(4-cyanophenyl)-1-(S)-(pyrrolidin-N-ylcarbonyl)eth-1-yl,
cyclohexyl,
cyclohexylmethyl,
2-(N-cyclopropylpiperidin-4-yl)eth-1-yl,
2-(N-cyclopropylpiperidin-4-y 1)-1-(R)-(pyrrolidin-N-ylcarbonyl)eth-1-yl,
1-(R)-1,3-di(benzyloxycarbonyl)prop-1-yl,
1-(S)-1,3-dicarboxamideprop-1-yl,
(2-dimethylamino)eth-1-yl,
2-[4-(N,N-dimethylamino]phenethyl,
3-(dimethylamino)prop-1-yl,
1-(S)-ethoxycarbonyleth-1-yl,
ethyl,
1-(R)-(1-N-ethylamino-carbonyl)-4-amino-n-butyl,
1-(S)-(1-N-ethylamino-carbonyl)-4-amino-n-butyl,
1-(R)-(1-N-ethylaminocarbonyl)-5-(t-butoxycarbonylamino)pent-5-yl,
1-(S)-(1-N-ethylaminocarbonyl)-5-(t-butoxycarbonylamino)pent-5-yl,
1-(R)-(1-N-ethylaminocarbonyl)-4-(N-t-butoxycarbonylamino)-n-but-5-yl,
1-(S)-(1-N-ethylaminocarbonyl)-4-(N-t-butoxycarbonylaniino)-n-but-5-yl,
1-(R)-(1-N-ethylaminocarbonyl)-5-guanadino-n-pent-5-yl,
1-(S)-(1-N-ethylaminocarbonyl)-5-guanadino-n-pent-5-yl,
1-R,S-(1-N-ethylaminocarbonyl)-4-(N-t-butoxycarbonyl)guanadino-n-but-1-yl,
1-(R)-(1-N-ethylaminocarbonyl)-5-(N-t-butoxycarbonylamino)-n-pent-5-yl,
1-(S)-(1-N-ethylaminocarbonyl)-5-(N-t-butoxycarbonylamino)-n-pent-5-yl,
4-fluorophenethyl,
hydrogen,
2-hydroxyeth-1-yl,
2-(4-hydroxyphenyl)-1-(S)-(methoxycarbonyl)eth-1-yl,
2-(4-hydroxyphenyl)-1-(S)-(isopropoxycarbonyl)eth-1-yl,
2-(4-hydroxyphenyl)-1-(R)-(methoxycarbonyl)eth-1-yl,
2-(N-hydroxypyrid-4-yl)eth-1-yl,
2-(imidazol-4-yl)eth-1-yl,
2-[4-(imidazolin-2-yl)phenyl]-1-(R)-(pyrrolidin-1-ylcarbonyl)eth-1-yl,
2-[4-(imidazolin-2-yl)phenyl]eth-1-yl,
2-(indol-3-yl)eth-1-yl,
2-(indol-3-yl)-1-(S)-(methoxycarbonyl)eth-1-yl,
2-(indol-3-yl)-1-(R)-(methoxycarbonyl)eth-1-yl,
iso-propyl,
1-(R)-(isopropoxycarbonyl)-2-(phenyl)eth-1-yl,
methoxy,
4-(methoxycarbonyl)benzyl,
1-(R)-(methoxycarbonyl)eth-1-yl,
methoxycarbonylmethyl,
methoxycarbonyiphenylmethyl,
2-methoxyeth-1-yl,
1-(R)-(methoxcarbonyl)-2-(N-methylpiperidin-4-yl)eth-1-yl,
1-(R)-(methoxycarbonyl)-2-(N-methyl-1,2,3,6-tetrahydropyrid-4-yl)eth-1-yl,
2-methoxyphenyl,
1-(R)-(methoxycarbonyl)-2-pyrid-4-yl)eth-1-yl,
methyl,
2-[4-(methylcarbonylamino]phenethyl,
1-(R)-(N-methyl-N-ethylcarbamoyl)-3-(guanadino)prop-1-yl,
2-(4-methylpiperazin-1-yl)eth-1-yl,
(N-methylpiperidin-2-yl)methyl,
2-(N-methylpiperidin-2-yl)eth-1-yl,
2-(N-methylpiperidin-3-yl)eth-1-yl,
2-(N-methylpiperidin-4-yl)eth-1-yl,
2-(N-methylpiperidin-4-yl)-1-(R)-(pyrrolidin-N-ylcarbonyl)eth-1-yl,
2-[(N-methyl)pyrrolidin-2-yl]eth-1-yl,
2-(N-methyl-1,2,5,6-tetrahydropyrid-4-yl)eth-1-yl,
2-(N-methyl-1,2,5,6-tetrahydropyrid-4-yl)-1-(R)-(pyrrolidin-N-ylcarbonyl)eth-1-yl,
3-(2-methylthiazol-5-yl)-pyrazol-5-yl,
2-(N-morpholino)eth-1-yl,
n-hexyl,
4-nitrobenzyl,
phenethyl, 1-(R)-phenyleth-1-yl,
1-(S)-phenyleth-1-yl,
phenyl,
4-phenylbut-1-yl,
1-(R)-2-phenylcarboxyeth-1-yl,
1-(R)-2-phenyl-1-(methoxycarbonyl)eth-1-yl,
1-(S)-2-phenyl-1-(methoxycarbonyl)eth-1-yl,
3-phenyl-n-prop-1-yl,
2-(phenyl)-1-(S)-(pyrrolidin-N-ylcarbonyl)eth-1-yl,
2-(piperidin-N-yl)eth-1-yl,
2-(piperidin-2-yl)eth-1-yl,
2-(piperidin-3-yl)eth-1-yl,
2-(piperidin-4-yl)eth-1-yl,
(piperid-1-yl)carbonylmethyl,
pyrazin-2-ylmethyl,
2-(pyrid-2-yl)eth-1-yl,
2-(pyrid-3-yl)eth-1-yl,
2-(pyrid-4-yl-)eth-1-yl,
(pyrid-2-yl)methyl,
(pyrid-3-yl)methyl,
(pyrid-4-yl)methyl,
2-[N-(pyrid-4-yl)]piperidin-4-yl,
2-[N-(pyrid-4-yl)piperid-4-yl)]eth-1-yl,
2-[N-(pyrid-2-yl)piperidin-4-yl]eth-1-yl
2-(pyrid-4-yl)-1-(R)-(pyrrolidin-N-ylcarbonyl)eth-1-yl,
1-(R)-(pyrrolidin-N-ylcarbonyl)-2-(4-amidino)phenyl-eth-1-yl,
1-(S)-(pyrrolidin-N-ylcarbonyl)-2-(4-amidino)phenyl-eth-1-yl,
1-(R)-(pyrrolidin-N-ylcarbonyl)-5-amino-n-pent-1-yl,
1-(S)-(pyrrolidin-N-ylcarbonyl)-5-amino-n-pent-1-yl,
1-(R)-(pyrrolidin-N-ylcarbonyl)-2-(4-biphenyl)eth-1-yl,
1-(S)-(pyrrolidin-N-ylcarbonyl)-2-(4-biphenyl)eth-1-yl,
1-(R)-(pyrrolidin-N-ylcarbonyl-2-(4-iodophenyl)eth-1-yl,
1-(S)-(pyrrolidin-N-ylcarbonyl-2-(4-iodophenyl)eth-1-yl,
1-(R)-(pyrrolidin-N-carbonyl)-4-(t-butoxycarbony-lamino)-n-but-1-yl,
1-(S)-(pyrrolidin-N-carbonyl)-4-(t-butoxycarbony-lamino)-n-but-1-yl,
1-(S)-(pyrrolidin-N-ylcarbonyl)-2-[4-(2-imidazolin-2-yl)phenyl]eth-1-yl,
2-(R)-(pyrrolidin-N-ylcarbonyl)-3-phenylprop-2-yl,
1-(R)-(pyrrolidin-N-ylcarbonyl)-2-[4-(N-methylpiperidin-2-yl)phenyl)]eth-1-yl
1-(S)-(pyrrolidin-N-ylcarbonyl)-2-[4-(N-methylpiperidin-2-yl)phenyl)]eth-1-yl
1-(R)-(pyrrolidin-N-ylcarbonyl)-2-[N-methyl-1,2,5,6-tetrahydropyridin-4-yl)-phen-4-yl)]eth-1-yl
1-(S)-(pyrrolidin-N-ylcarbonyl)-2-[N-methyl-1,2,5,6-tetrahydropyridin-4-yl)-phen-4-yl)]eth-1-yl
1-(R)-(pyrrolidin-N-ylcarbonyl)-2-[4-(piperidin-2-yl)cyclohexyl)]eth-1-yl,
1-(S)-(pyrrolidin-N-ylcarbonyl)-2-[4-(piperidin-2-yl)cyclohexyl)]eth-1-yl,
1-(R)-(pyrrolidin-N-ylcarbonyl)-2-[N-(phenyl)piperidin-4-yl)]eth-1-yl
1-(S)-(pyrrolidin-N-ylcarbonyl)-2-[N-(phenyl)piperidin-4-yl)]eth-1-yl
1-(R)-(pyrrolidin-N-ylcarbonyl)-2-[N-(pyridin-4-yl)piperidin-4-yl)]eth-1-yl
1-(S)-(pyrrolidin-N-ylcarbonyl)-2-[N-(pyridin-4-yl)piperidin-4-yl)]eth-1-yl
1-(R)-(pyrrolidin-N-ylcarbonyl)-2-[4-(pyridin-4-yl)phenyl)]eth-1-yl
1-(S)-(pyrrolidin-N-ylcarbonyl)-2-[4-(pyridin-4-yl)phenyl)]eth-1-yl
1-(R)-(pyrrolidin-N-ylcarbonyl)-2-[4-(pyrid-2-yl)phenyl]eth-1-yl,
1-(S)-(pyrrolidin-N-ylcarbonyl)-2-[4-(pyrid-2-yl)phenyl]eth-1-yl,
1-(R)-(pyrrolidin-N-ylcarbonyl)-2-[4-(pyrimidin-2-yl)phenyl]eth-1-yl,
1-(S)-(pyrrolidin-N-ylcarbonyl)-2-[4-(pyrimidin-2-yl)phenyl]eth-1-yl,
1-(R)-(pyrrolidin-N-ylcarbonyl)-2-[4-(N-t-butoxycarbon-ylpyrrol-2-yl)phenyl]eth-1-yl,
1-(S)-(pyrrolidin-N-ylcarbonyl)-2-[4-(N-t-butoxycarbon-ylpyrrol-2-yl)phenyl]eth-1-yl,
1-(S)-(t-butoxycarbonyl)-2-(4-hydroxyphenyl)eth-1-yl,
3-t-butoxycarbonyl-1-methoxycarbonyiprop-1-yl,
2-[N-(t-butoxycarbonylmethyl)piperid-4-yl]eth-1-yl,
2-[1-(t-butoxycarbonylmethyl)piperid-4-yl)]eth-1-yl,
1-(S)-(t-butoxycarbonyl)-3-methylprop-1-yl,
1-(R)-(t-butoxycarbonyl)-3-methylprop-1-yl,
1-(R)-(t-butoxycarbonyl)-2-(phenyl)eth-1-yl,
2-cyclopropyl-2-(pyridin-4-yl)eth-1-yl, and
2-(N-t-butoxycarbonylmethyl)pyridin-4-yl-ethyl.

5. A compound of the formula:

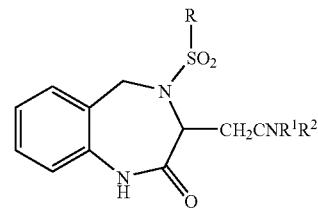

wherein
R is selected from the group consisting of aryl, substituted aryl, heteroaryl, substituted heteroaryl, heterocyclic and substituted heterocyclic; and
$R^1$ and $R^2$, together with the nitrogen atom bound thereto, are joined to form a heterocyclic or substituted heterocyclic group; or
pharmaceutically acceptable salts, tautomers or isomers thereof.

6. A compound according to claim 5 wherein R is selected from the group consisting of phenyl; naphth-1-yl; 5-dimethylamino-naphth-1-yl; 2-fluorophenyl; 2-chlorophenyl; 2-cyanophenyl; 2-methylphenyl; 2-nitro-phenyl; 2-trifluoromethylphenyl; 3-chlorophenyl; 4-methylphenyl (tolyl); 2,5-dibromophenyl; 4-bromo-2-ethylphenyl; 4-bromo-2-trifluoromethoxy-phenyl; 2,3-dichlorophenyl; 2,4-dichlorophenyl; 3,4-dichlorophenyl; 2,5-dichlorophenyl; 3,5-dichlorophenyl; 2,6-dichlorophenyl; 2-chloro-4-cyanophenyl; 2-chloro-4-fluorophenyl; 3-chloro-2-methylphenyl; 2-chloro-6-methylphenyl; 5-chloro-2-methoxyphenyl; 2-chloro-4-trifluoromethyl-phenyl; 2,4-difluorophenyl; 5-fluoro-2-methylphenyl; 2,5-dimethoxyphenyl; 2-methoxy-4-methylphenyl; 2-methoxy-5-bromophenyl; 2-methoxy-5-methylphenyl; 2,5-dimethylphenyl; 2-methyl-5-nitrophenyl; 3,5-di(trifluoro-methyl)phenyl; 4-bromo-2,5-difluorophenyl; 2,3,4-trichlorophenyl; 2,4,5-trichlorophenyl; 2,4,6-trichlorophenyl; 2,4-dichloro-5-methylphenyl; 4-chloro-2,5-dimethylphenyl; 2,4,6-tri(iso)propylphenyl; 2,4,6-trimethyl-phenyl; 2,3,5-trimethyl-4-chlorophenyl; 2,3,6-trimethyl-4-methoxyphenyl; 2,3,4,5,6-pentamethylphenyl; 5-chloro-1,3-dimethylpyrazol-4-yl; 2-methoxy-carbonyl-thiophen-3-yl; 2,3-dimethylimidazol-5yl; 2-methylcarbonylamino-4-methyl-thiazol-5-yl; quinolin-8-yl; thiophen-2-yl; 1-methylimidiazol-4-yl; 3,5-dimethylisoxazol-4-yl; and N-morpholino.

7. The compound according to claim 6 wherein R is selected from the group consisting of 4-chloro-2,5-dimethylphenyl and 2,3-dichlorophenyl.

8. The compound according to claim 1 wherein $R^1$ and $R^2$, together with the nitrogen atom bound thereto, form a substituted heterocyclic group.

9. The compound according to claim 8, wherein the substituted heterocyclic group is selected from the group consisting of 4-(2-aminoethyl)piperidin-1-yl, 4-[2-(N-t-butoxycarbonylamino)ethyl]piperidin-1-yl, N-morpholino, 2-methylpiperid-N-yl, 2-(S)-carboxamide-pyrrolidin-N-yl, 2-(R)-hydroxy-5-(S)-methoxy-carbonylpyrrolidin-N-yl, 2-(R)-methoxycarbonyl-pyrrolidin-N-yl, 2-(S)-methoxymethyl-pyrrolidin-1-yl, 3-(R)-(t-butoxycarbox-amido)pyrrolidin-N-yl, 3-carboxamido-piperid-N-yl, 3-hydroxypyrrolidin-N-yl, 4-acetyl-piperazin-1-yl, 4-hydroxypiperid-N-yl, 4-methylpiperazin-1-yl, 4-(pyridin-4-yl)piperazin-1-yl, and 2-methoxycarbonylpyrrolidin-N-yl, 4-(pyridin-2-yl)piperzin-1-yl and 4-(pyridin-4-yl)piperazin-1-yl.

10. The compound according to claim 8 wherein the substituted heterocyclic group is selected from the group consisting of 4-(pyridin-2-yl)piperazin-1-yl and 4-(pyridin-4-yl)piperazin-4-yl.

11. A compound selected from the group consisting of:
- 3-[3-(R,S)-(4-chloro-2,5-dimethylbenzenesulfonyl)-4-oxo-2,5-benzodiazepin-3-yl]-N-[2-(pyridin-4-yl)ethyl]acetamide;
- 3-[3-(R,S)-(4-chloro-2,5-dimethylbenzenesulfonyl)-4-oxo-2,5-benzodiazepin-3-yl]-N-[2-(1,2,3,6-tetrahydro-N-methylpyridin-4-yl)eth-1-yl]acetamide;
- 3-[3-(R,S)-(4-chloro-2,5-dimethylbenzenesulfonyl)-2-oxo-2,5-benzodiazepin-3-yl]-N-[2-(N-methylpiperidin-4-yl)eth-1-yl]acetamide;
- 3-[3-(R,S)-(4-chloro-2,5-dimethylbenzenesulfonyl)-2-oxo-2,5-benzodiazepin-3-yl]-N-[2-(N-{pyrid-4-yl}piperidin-4-yl)eth-1-yl]acetamide;
- 3-[3-(R,S)-(4-chloro-2,5-dimethylbenzenesulfonyl)-2-oxo-2,5-benzodiazepin-3-yl]-N-[2-(N-oxopyridin-4-yl)eth-1-yl]acetamide;
- 3-[3-(R,S)-(4-chloro-2,5-dimethylbenzenesulfonyl)-2-oxo-2,5-benzodiazepin-3-yl]-N-[4-(pyridin-2-yl)piperazin-1-yl]acetamide;
- 3-[3-(R,S)-(4-chloro-2,5-dimethylbenzenesulfonyl)-2-oxo-2,5-benzodiazepin-3-yl]-N-[4-(pyridin-4-yl)piperazin-1-yl]acetamide;
- 3-[3-(R,S)-(4-chloro-2,5-dimethylbenzenesulfonyl)-2-oxo-2,5-benzodiazepin-3-yl]-N-[2-cyclopropyl-2-(pyridin-4-yl)eth-1-yl]acetamide;
- 3-[3-(R)-(4-chloro-2,5-dimethylbenzenesulfonyl)-4-oxo-2,5-benzodiazepin-3-yl]-N-[2-(pyridin-4-yl)ethyl]acetamide;
- 3-[3-(S)-(4-chloro-2,5-dimethylbenzenesulfonyl)-4-oxo-2,5-benzodiazepin-3-yl]-N-[2-(pyridin-4-yl)ethyl]acetamide;
- 3-[3-(R,S)-(2,3-dichlorobenzenesulfonyl)-2-oxo-2,5-benzodiazepin-3-yl]-N-[2-(R,S)-cyclopropyl-2-(pyridin-4-yl)eth-1-yl]acetamide;
- 3-[3-(R,S)-(2,3-dichlorobenzenesulfonyl)-4-oxo-2,5-benzodiazepin-3-yl]-N-[2-(pyridin-4-yl)ethyl]acetamide;
- 3-[3-(R,S)-(2,3-dichlorobenzenesulfonyl)-2-oxo-2,5-benzodiazepin-3-yl]-N-[2-(N-{pyridin-2-yl}piperidin-4-yl)eth-1-yl]acetamide; and
- 3-[3-(R,S)-(4-chloro-2,5-dimethylphenylcarbonylmethyl)-2-oxo-2,5-benzodiazepin-3-yl]-N-[2-pyridin-4-yleth-1-yl]acetamide;

or a pharmaceutically acceptable carrier and a therapeudic amount of a compound according to any one of claims 1, 5, or 11.

12. A pharmaceutical composition comprising a pharmaceutically acceptable carrier and a therapeutically amount of a compound according to claims 1, 5, and or 11.

* * * * *